US007251643B2

(12) United States Patent
Gange et al.

(10) Patent No.: US 7,251,643 B2
(45) Date of Patent: Jul. 31, 2007

(54) SYSTEM, APPARATUS, AND METHOD FOR USER TUNABLE AND SELECTABLE SEARCHING OF A DATABASE USING A WEIGHTED QUANTIZED FEATURE VECTOR

(75) Inventors: David M. Gange, Pennington, NJ (US); Bomi Patel Framroze, Bombay (IN)

(73) Assignee: Row2 Technologies, Inc., Parsippany, NJ (US)

( * ) Notice: Subject to any disclaimer, the term of this patent is extended or adjusted under 35 U.S.C. 154(b) by 61 days.

(21) Appl. No.: 10/516,061

(22) PCT Filed: May 25, 2004

(86) PCT No.: PCT/US2004/016322

§ 371 (c)(1),
(2), (4) Date: Nov. 29, 2004

(87) PCT Pub. No.: WO2004/107217

PCT Pub. Date: Dec. 9, 2004

(65) Prior Publication Data

US 2006/0074859 A1 Apr. 6, 2006

Related U.S. Application Data

(63) Continuation-in-part of application No. 10/448,168, filed on May 28, 2003.

(51) Int. Cl.
*G06F 17/30* (2006.01)
(52) U.S. Cl. .......................................................... 707/1
(58) Field of Classification Search ................ 707/2–4, 707/5, 6, 10, 104.1, 1; 345/156
See application file for complete search history.

(56) References Cited

U.S. PATENT DOCUMENTS 6,094,648 A * 7/2000 Aalbersberg ................... 707/3
6,433,771 B1 * 8/2002 Yocum et al. ................ 345/156
2002/0019819 A1 * 2/2002 Sekiguchi et al. .............. 707/3

OTHER PUBLICATIONS

Peter Willet et al., Chemical Similarity Searching, Feb. 1998, American Chemical Society, pp. 983-996.*

* cited by examiner

*Primary Examiner*—Etienne P. LeRoux
(74) *Attorney, Agent, or Firm*—Stanley H. Kremen

(57) ABSTRACT

A data processing means for user tunable and selectable (FIG. 2) of a database wherein the data contained therein have associated descriptive properties (FIG. 2) capable of being expressed in numeric form is described. Descriptive property values (FIG. 2) may be standardized numerically to eliminate property value overweighting. A quantized vector (FIG. 2) representative of the descriptive properties is created for each item in the database. This quantized vector becomes the fingerprint for each data item. The user submits a query item to be matched against the database for similarity. A fingerprint is calculated for the query item. The user may then assign weights to the individual descriptive properties based upon perceived importance (FIG. 2). A newly weighted fingerprint for the query item is then compared with the fingerprints for all the data in the database. A list of results is presented to the user (FIG. 2). The user may then change the previously assigned weights and then re-run the similarity search. This may be done as often as necessary to achieve the desired results. Similarity searching in a generic database is described. However, particulary the method is desirable in databases containing chemical compound structure data or biological response screening result data.

105 Claims, 18 Drawing Sheets

| Spectral Tranformation Matrix | | | | | | | | | | | |
|---|---|---|---|---|---|---|---|---|---|---|---|
| 0.29 | 0.71 | 0.41 | 0.29 | 0.22 | 0.18 | 0.15 | 0.13 | 0.11 | 0.11 | 0.10 | 0.09 |
| 0.29 | -0.71 | 0.41 | 0.29 | 0.22 | 0.18 | 0.15 | 0.13 | 0.11 | 0.11 | 0.10 | 0.09 |
| 0.29 | 0.00 | -0.82 | 0.29 | 0.22 | 0.18 | 0.15 | 0.13 | 0.11 | 0.11 | 0.10 | 0.09 |
| 0.29 | 0.00 | 0.00 | -0.87 | 0.22 | 0.18 | 0.15 | 0.13 | 0.11 | 0.11 | 0.10 | 0.09 |
| 0.29 | 0.00 | 0.00 | 0.00 | -0.89 | 0.18 | 0.15 | 0.13 | 0.11 | 0.11 | 0.10 | 0.09 |
| 0.29 | 0.00 | 0.00 | 0.00 | 0.00 | -0.91 | 0.15 | 0.13 | 0.11 | 0.11 | 0.10 | 0.09 |
| 0.29 | 0.00 | 0.00 | 0.00 | 0.00 | 0.00 | -0.93 | 0.13 | 0.11 | 0.11 | 0.10 | 0.09 |
| 0.29 | 0.00 | 0.00 | 0.00 | 0.00 | 0.00 | 0.00 | -0.94 | 0.11 | 0.11 | 0.10 | 0.09 |
| 0.29 | 0.00 | 0.00 | 0.00 | 0.00 | 0.00 | 0.00 | 0.00 | -0.94 | 0.11 | 0.10 | 0.09 |
| 0.29 | 0.00 | 0.00 | 0.00 | 0.00 | 0.00 | 0.00 | 0.00 | 0.00 | -0.95 | 0.10 | 0.09 |
| 0.29 | 0.00 | 0.00 | 0.00 | 0.00 | 0.00 | 0.00 | 0.00 | 0.00 | 0.00 | -0.95 | 0.09 |
| 0.29 | 0.00 | 0.00 | 0.00 | 0.00 | 0.00 | 0.00 | 0.00 | 0.00 | 0.00 | 0.00 | -0.96 |

FIG. 12(c)

SYSTEM, APPARATUS, AND METHOD FOR USER TUNABLE AND SELECTABLE SEARCHING OF A DATABASE USING A WEIGHTED QUANTIZED FEATURE VECTOR

CROSS REFERENCE TO RELATED APPLICATIONS

This application is the U.S. nonprovisional National Stage Application, filed in accordance with 35 U.S.C. 371, that is a U.S. counterpart of and claims priority to PCT Application serial No. PCT/US04/16322 having an international filing date of May 25, 2004, entitled SYSTEM, APPARATUS, AND METHOD FOR USER TUNABLE AND SELECTABLE SEARCHING OF A DATABASE USING A WEIGHTED QUANTIZED FEATURE VECTOR, still pending, said PCT Application being a continuation-in-part (CIP) of and claiming priority to U.S. nonprovisional application Ser. No. 10/448,168 filed on May 28, 2003, entitled SYSTEM, APPARATUS, AND METHOD FOR USER TUNABLE AND SELECTABLE SEARCHING OF A DATABASE USING A WEIGHTED QUANTIZED FEATURE VECTOR, still pending, and published as U.S. Patent Application Publication No. 2004/0006559 A1, being the U.S. nonprovisional utility patent application that is also described in and claims the benefit of both U.S. provisional patent application 60/383,952 filed on May 29, 2002, entitled MACHINE, METHOD AND ARTICLE OF MANUFACTURE FOR ASELECTIVELY SEARCHING A DATABASE OF CHEMICAL COMPOUNDS, and Ser. No. 60/384,305 filed on May 30, 2002, entitled MACHINE, METHOD AND ARTICLE OF MANUFACTURE FOR SEARCHING A DATABASE OF BIOLOGICAL ACTIVITY SCREENING RESULTS, said provisional applications being incorporated by reference in their entirety herein.

FIELD OF THE INVENTION

This invention relates to data processing and specifically enabling highly efficient searching of a database wherein the entries can be characterized using a set of one or more descriptive properties that can be expressed in numeric form.

BACKGROUND OF THE INVENTION

Modern database management systems have been used since the early 1970's. Commercial database systems mostly concentrate on finding exact matches. Searches are performed either to find a specific entry, or to find multiple entries having the same characteristics. Attributes of the data often become fields. An exact search can be made to find a specific person by looking up his name or social security number. A search can be performed to find multiple individuals having the same occupation or place of birth. Alternatively, one may locate all people born before a particular date. Whether a single entry or multiple entries are found, this type of query constitutes an exact search. Exact searches try to exactly or relationally match one or more fields in different data records.

Similarity searching of databases has been around for several years. A similarity search compares two or more entries in their entirety to determine how closely they match one another. Consider the following simple database containing entries of various animals that fly:

a house-fly
a bat
a hummingbird
a dragonfly
a flying fish
a hawk

The question: "Which are most similar?" is not meaningful without additional input. A proper answer requires input of the key dimension. If "feathers" represent the key dimension, then the hawk and the hummingbird are most similar. If "the ability to fly stationary" is the key dimension, then the dragonfly and the hummingbird are most similar. Other possible key dimensions could be metabolism, life span, body temperature, etc. Therefore, the answer to the question: "Which are most similar?" is subjective depending upon the preferences of the person asking the question.

For a more complicated residential real estate database, a potential buyer would be looking to buy a home by expressing preferences that become the parameters for a similarity search. Such parameters might include number of bedrooms, type of house, asking price, neighborhood, quality of the local school system, property taxes, age restrictions on residents, home-owners' associations, etc. Currently, a real estate agent would first screen for homes having a specific most desirable characteristic (e.g., neighborhood or number of bedrooms). Then, the agent would look for the next desirable characteristic. The process would be repeated for each parameter, each search yielding a number of homes for consideration by the buyer. Where a particular home appears in the search results multiple times, it is more likely that the agent can make a sale. However, a feature vector may be created using these and other parameters, and a similarity search can be performed to match a potential buyer's preferences. This search would generate a list of homes approximating these preferences. A vector could indicate whether or not the buyer is interested in a particular feature. The homes can then be compared in their entirety by computing the mathematical difference between their feature vectors. The smaller the difference between the feature vectors of an ideal home and an available home, the more similar they are.

Representations of organic chemical compounds can be structurally decomposed into recognizable fragments, such as functional groups, carbocyclic rings, heterocyclic rings, aliphatic chains, and carbon-heteroatom chains. Many databases store molecular information according to their chemical structure fragments. The data processing systems maintain a fragment dictionary, and all compounds input into the database are parsed so as to generate a descriptor vector of each compound. Each element in the descriptor vector corresponds to a fragment in the fragment dictionary. The dictionary is instituted with fragments well known to those skilled in the art.

In other chemical database systems an algorithm replaces the chemical fragment dictionary. Such algorithms, in effect, generate chemical fragments on the fly and the fragments are then used to parse chemical structures and create a descriptor vector. The elements of the vector may directly correspond to chemical fragments or an algorithm, such as a hashing algorithm, may be used to generate an alternative relationship between the compounds and the vector elements.

One possible representation of a molecule would be to parse it into a binary fragment vector. Each bit represents the presence or absence of a particular fragment in the fragment dictionary or fragment generating algorithm. The binary vector may be represented logically as a string of bits or bytes or may have any convenient representation. The binary vector forms a fingerprint for the molecule. Each bit or fragment in the fingerprint is a dimension representing one row in the vector.

A chemical structure similarity search may be performed by calculating the similarity between the vector for a query compound and the vectors of the compounds stored in a chemical database. Standard measures of similarity such as Euclidean Distance, Tanimoto coefficient, Hamming Distance, Soergel Distance, Dice Coefficient, Cosine Coefficient or other similarity algorithms can be used for the similarity calculation. The results can then be returned in order of decreasing similarity.

In another application, chemical compounds, natural products, fermentation broths, and other substances are often tested for biological activity, or pharmacological activity. The results of these tests are often stored in electronic databases. One method that can be used to examine biological screening results and property data is similarity searching. A biological activity profile can be created by graphing the test results of a specific compound in multiple biological tests. Compounds possessing a similar mode of action often possess similar biological profiles. Biologists and chemists are thus often interested in searching a database of biological screening results for substances with an activity profile similar to a given biological activity profile. For example, in the development of an antibiotic a scientist might be interested in substances showing good activity against gram-positive bacteria and one species of gram-negative bacteria. The profile of such a substance would have strong activity values for the several gram-positive and one gram-negative bacteria under consideration and weak activity values for the rest of the gram-negative species tested. In addition to biological activity descriptors, chemical descriptors may be usefully included in the description of a compound. Chemical structure descriptors, as discussed above, or properties such as pKa (acidity/basicity), LogP (lipophilicity measurement), MR (molar refractivity), IR (index of refraction), hydrogen bond donor count, hydrogen bond acceptor count, heteroatom count, molecular weight, Rule of 5 value (Lipinski value), retention value (measured via gas chromatography, liquid chromatography, or thin layer chromatography), or spectroscopic peak measurements (infrared, nuclear magnetic resonance, ultraviolet) may be used to characterize the compounds. These descriptors can be included in compound fingerprints and used in both chemical and biological similarity calculations.

In this case, it would be desirable to create a vector where a specific element would refer to a particular feature or test, and the vector would contain numeric values. The difference between vectors may be measured, and difference values would represent the degree of similarity between entries in the database.

Variables may be standardized prior to performing the similarity calculations to insure that all variables are treated equally. For example, variables may be mean-centered and scaled to unit variance according to procedures that are well known in statistical art. (For example, see Weisberg, S., "Applied Linear Regression," Second Edition, John Wiley and Sons, 1985, pp 185–186.) For a vector X with j elements:

$$\frac{X_j - \bar{x}_j}{SD_j}$$

where:
$\bar{x}_j$=mean of the elements of X, and
$SD_j$=standard deviation of the elements of X.

Other standardization techniques well known in the statistical art are also used.

Similarity searching using vectors is prior art. The similarity between vectors may be measured, and magnitude of the similarity value would represent the degree of similarity between entries in the database. In current systems the results of the similarity calculations are, to a large extent, predetermined by the algorithm. However, a user of a similarity searching system may have different ideas about the importance of various descriptors that are used in the similarity calculation. For example, when chemists search for similarity in chemical compounds, some parts of the molecule are more important to them than other parts. A chemist may be searching for compounds whose biological activity is similar, or they may be searching for compounds whose syntheses are similar. The importance of fragment descriptors will vary depending upon the type of similarity sought. Chemists therefore, when performing a search, would be interested in establishing a higher search priority for the fragment descriptors they consider important and a lower search priority for the other fragment descriptors. Currently search priorities are defined by the search algorithm designer. It priorities of descriptors can be dynamically assigned by the user, then the results of the search will reflect what user desires. The units of assigned priority or weights can be arbitrary, and only their ratio to each other is important.

Another issue for scientists using chemical structure similarity searching is the need to perform multiple searches in order to find all relevant answers. Certain chemical functional groups, while structurally different, are known in the art to be similar to one another. For example, the syntheses of common heterocycles are often similar. A scientist searching for information related to the synthesis of one heterocycle might also be interested in the syntheses of related similar heterocycles. In addition, it is well known in the art that certain functional groups (bio-isosteres) often possess similar biological effects, even if they differ at the atomic level. For example, sulfonamide can often be substituted for carboxylic acid in biologically active compounds. Current similarity calculations based upon molecular structure do not take synthetic similarity or bio-isosteric similarity into account. If a scientist wishes to search for all of the compounds that are of interest, multiple queries must be entered and searched. Automation of secondary query generation and searching would simplify the task of the user.

In the previously mentioned residential real estate database, the similarity search revealed homes having all of the features that interested a potential buyer. Yet, for some potential buyers, certain items are more important than others. For example, for a family with four children, purchase of a house with five bedrooms and the quality of the school system might be more important than asking price and property taxes. Yet these latter features could also serve as influencing factors. In such a case, being able to assign higher priorities to certain features and lower priorities to other features would result in a more meaningful search.

It is important to note that where various fields in a data record are not numerically related to each other, the variations in their magnitude may be large thereby improperly biasing the search. In the example of the residential real estate database, the price of a house is represented by a very much larger number than the number of bedrooms in the house. If the data record is not standardized as mentioned earlier, the price will dominate the similarity calculation even where the number of rooms has a higher priority. By mean-centering the data fields and scaling them to unit variance, a more meaningful search can be performed.

The underlying mathematics for searching is very broadly applicable. It can be used inter alia in biology and medical databases, in physiology databases, in anthropology databases, in photography databases, and in taxonomy databases. It is practical where a characterization vector can be applied to the description of the data.

It is an object of the invention described herein to create a computerized system that will perform similarity searches in an electronic database where the entries have a set of one or more descriptive properties capable of being expressed in numeric form and wherein the user can assign weights or priorities to the descriptive properties so as to influence the similarity searches. It is a further object of the invention to provide a means for the generation of secondary queries from a primary query to insure that other relevant similar entries are retrieved from the database.

SUMMARY OF THE INVENTION

The invention disclosed herein is a data processing product and method that permits computerized similarity searching of an electronic database using a vector. The vector, a linear array of descriptors of the entries in the database, is maintained by the system. Different datatype representations of the vector may be implemented. The system examines the structure of a query item in terms of its known descriptors. During examination, the vector is established. This vector represents the query item's "fingerprint." The system then searches the entire database for identity or similarity to the query item by comparing the vectors. The system further permits the user to set numeric priorities for the descriptors in a user friendly environment, said priorities to be used in the search for entries that are similar to the query item. An object of the invention is to provide a simplified searching system for naive and infrequent users. In one of the embodiments presented herein, a computerized user-tunable system is disclosed that selectively searches a database of chemical compounds. In another embodiment presented herein, a computerized user-tunable system is disclosed that selectively searches a database of biological activity screening test results.

BRIEF DESCRIPTION OF THE DRAWINGS

FIG. 12 is a MICROSOFT EXCEL spreadsheet divided into three parts, FIG. 12(*a*), (*b*), and (*c*), done so because the entire spreadsheet could not conveniently fit on a single drawing sheet. The data represented in the spreadsheet (the LEWI Data) represents the biological response test data of rats to various tranquilizers.

DESCRIPTION OF THE PREFERRED AND ALTERNATE EMBODIMENTS

One embodiment of the present invention comprises a database and a client system capable of interfacing with the database. The client system is connected to the database through a modem or LAN or WAN or wireless network or other communication network.

Figure 1:
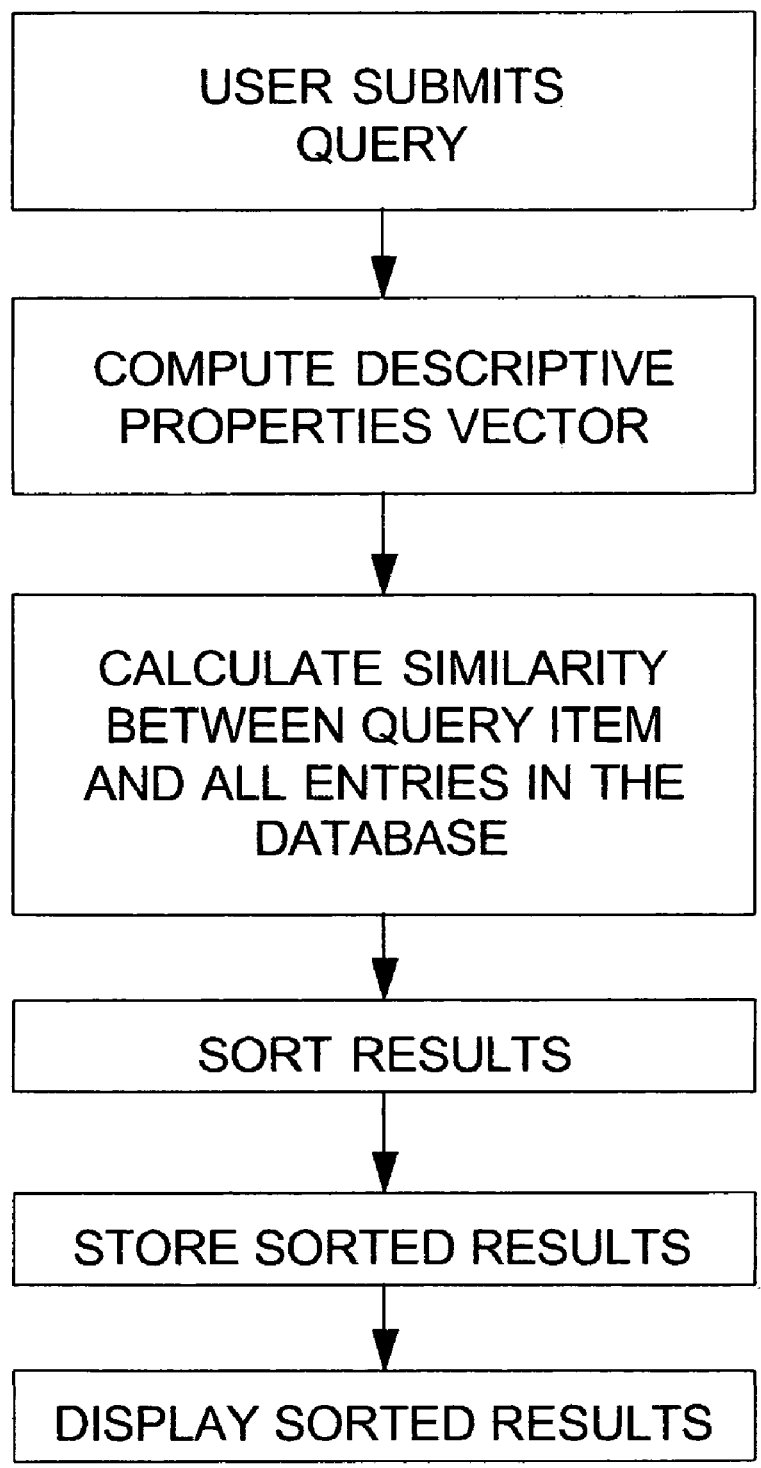
FIG. 1 is an overview program flowchart showing a current computerized method of performing similarity searches for a generalized database. The method shown is prior art.

It is feasible to perform similarity searches in an electronic database of items, wherein said items possess a set of one or more descriptors (related to the items) that can be expressed in numeric form. Similarity searching in such a generalized database according to current technology may be performed in a computer using the method shown in FIG. 1.

1. A user submits a query to the system. The query may be submitted using different formats, but a query item must be able to be classified according to its descriptive properties. The descriptive properties may have inherent numeric values (e.g., test results, characteristic values, prices, ASCII values, checksums, etc.). Alternatively, they may have binary values ('one' indicating the presence of a feature and 'zero' indicating the absence of the feature).

2. The query item is parsed to determine the value of its descriptive properties. The characteristics of these descriptive properties may be pre-stored in an electronic dictionary or they may be generated dynamically by some program algorithm, or both. The query item is analyzed for value of a particular property, and its numeric value is noted. A quantized vector is formed wherein each element in the vector represents a value for a specific descriptive property. The quantized vector can be thought of as a "fingerprint" for the query item.

3. The database contains entries of similarly describable items, each such item having been similarly pre-parsed into quantized vectors. The quantized vector (or "fingerprint") for each entry is stored in the database and associated with its entry. Therefore, a difference may be computed between the vector representing the query item and each vector representing each and every item in the database. The smaller the difference between the query item vector and a vector representing an entry in the database, the more similar the query item is to that database entry.
4. The results are sorted in order of similarity.
5. The sorted results may be stored for future use at the user's discretion.
6. The sorted list of database entries is then presented to the user.

The computation of vector distances in step 3 above may be calculated, inter alia, as the standard Euclidean Distance, the Tanimoto Coefficient, the Hamming Distance, the Soergel Distance, the Dice Coefficient, or the Cosine Coefficient. Other types of similarity measurement may also be used.

The most familiar method for computing the distance between two vectors, thereby comparing their overall similarity, is to measure the Euclidean distance between them. This is done according to the well known equation:

$$D_{A,B} = \left[ \sum_{j=1}^{j=n} (x_{jA} - x_{jB})^2 \right]^{\frac{1}{2}} \quad [1]$$

where:

$D_{A,B}$=the distance between vectors A and B;
j=the index to a specific vector element;
n=the number of elements in the vector;
$x_{jA}$=the value of the jth element in the A vector; and,
$x_{jB}$=the value of the jth element in the B vector.

This is the familiar process of obtaining the difference between each of the elements in the same position in each vector, squaring that difference, and then taking the square root of the sum of the squares. Using this method, the distance between two identical vectors would be zero. The smaller the distance between two vectors, the greater their degree of similarity. The Euclidean Distance can be normalized to the range of 0 to 1 if the values of all attributes are normalized to this range and the results divided by n.

To illustrate computation of the distance, assume two binary dimension 5 vectors: A=1 1 0 1 1 and B=0 1 1 1 0. Using Equation [1], the calculation of Euclidean distance from A to B is as follows:

| A − B = C | | | C * C | Sum of C | Distance |
|---|---|---|---|---|---|
| 1 | 0 | 1 | 1 | 3 | 1.73 |
| 1 | 1 | 0 | 0 | | |
| 0 | 1 | −1 | 1 | | |
| 1 | 1 | 0 | 0 | | |
| 1 | 0 | 1 | 1 | | |

Another method for comparing similarity is to compute the Tanimoto Coefficient of the two vectors. This is done using the equation:

$$S_{A,B} = \frac{\sum_{j=1}^{j=n} x_{jA} x_{jB}}{\sum_{j=1}^{j=n} (x_{jA})^2 + \sum_{j=1}^{j=n} (x_{jB})^2 - \sum_{j=1}^{j=n} x_{jA} x_{jB}} \quad [2]$$

where:

$S_{A,B}$=the Tanimoto Coefficient.

The Tanimoto Coefficient is determined by taking the quotient of the sum of the cross product of two vectors divided by the sum of the squares of the elements of the first vector added to the sum of the squares of the elements of the second vector less the cross product of the two vectors. Another name for the Tanimoto Coefficient is the Jaccard Coefficient.

Other distance computations such as the Hamming Distance, the Soergel Distance, the Dice Coefficient and the Cosine Coefficient are sometimes used to perform similarity searches and are prior art. The Hamming Distance is computed as:

$$D_{A,B} = \sum_{j=1}^{j=n} |x_{jA} - x_{jB}| \quad [3]$$

The Soergel Distance is computed as:

$$D_{A,B} = \frac{\sum_{j=1}^{j=n} |x_{jA} - x_{jB}|}{\sum_{j=1}^{j=n} \max(x_{jA} \cdot x_{jB})} \quad [4]$$

The Dice Coefficient (also known as the Czekanowski Coefficient and the Sørenson Coefficient) is computed as:

$$S_{A,B} = \frac{2 \sum_{j=1}^{j=n} x_{jA} x_{jB}}{\sum_{j=1}^{j=n} (x_{jA})^2 + \sum_{j=1}^{j=n} (x_{jB})^2} \quad [5]$$

The Cosine Coefficient is computed as:

$$S_{A,B} = \frac{2 \sum_{j=1}^{j=n} x_{jA} x_{jB}}{\left[ \sum_{j=1}^{j=n} (x_{jA})^2 \sum_{j=1}^{j=n} (x_{jB})^2 \right]^{1/2}} \quad [6]$$

The foregoing comparison methodologies represented by Equations [1] through [6] are only a few prior art techniques for similarity measurement between two quantized vectors. Of course, the measure of similarity depends upon the descriptors chosen. Changing the "fingerprint" changes the similarity. The results are dictated by the algorithm of the system. For the aforementioned prior art similarity measurement methods, there is generally no feedback, no user control over the results, and no possibility of iteratively improving the answer.

Figure 2:
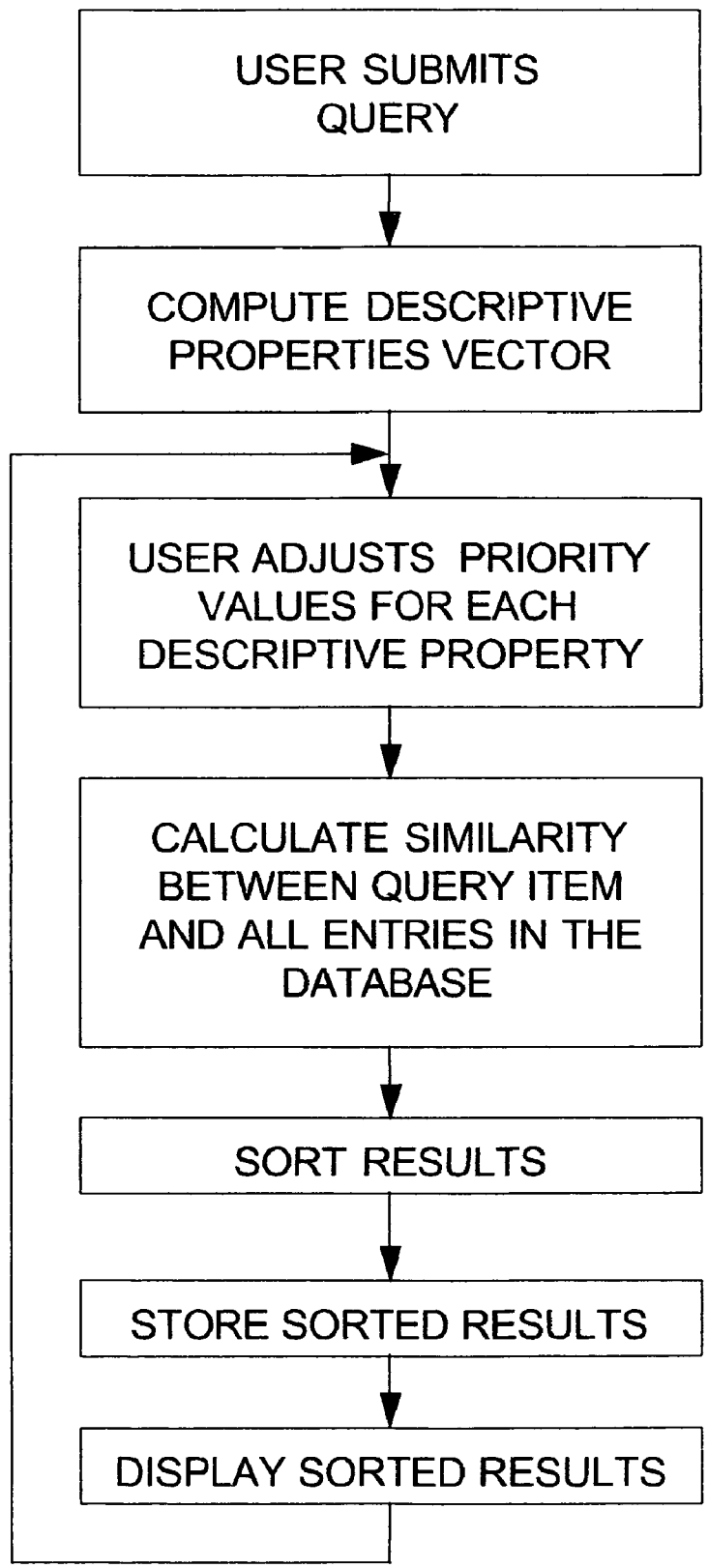
FIG. 2 is an overview program flowchart showing the computerized method of the invention disclosed herein being used to perform similarity searches for a generalized database.

The present invention improves the quality of the results obtained from similarity searching in the type of database discussed above. The results obtained from a search using the methodology disclosed herein should be more meaningful to the user. FIG. 2 is an overview program flowchart showing the computerized method of the invention disclosed herein being used to perform similarity searches for a generalized database. The methodology is as follows:

1. The user submits a query item to the system either directly or via a network connection using a modem or LAN or WAN or wireless network or other communication network.
2. The query item is parsed to determine the value of its descriptive properties using the same method that is used to calculate the descriptive properties of the entries stored in the database. A quantized vector (or "fingerprint") for the query item is formed.
3. The query item and its descriptor vector elements are communicated back to the user. The user is then permitted to assign a weight or priority to each descriptor, or element, in the query vector. The assignment of weights can be done by presenting to the user a computer screen showing the query item, the descriptors of the query item, and a means to adjust weighting to assign importance values to the descriptors. The means to adjust weighting may be adjustable sliders, dials, text boxes, or any other controls that permit the user to interactively assign weights to the descriptors. Alternatively, the weight values representing the elements of the weighting vector may be obtained from a file. A weighting vector is then formed in this manner. The weighting vector has the same dimension (or number of elements) as the vector representing the fingerprint of the query item.
4. Using the query item properties and weightings, similarity values between the query item and all of the items in the database are calculated using one of the standard similarity algorithms (Euclidean Distance, Tanimoto Coefficient, etc.)
5. Using the calculated similarity values, the database items are sorted.
6. The sorted results may be stored for future use at the user's discretion.
7. The sorted list of database items is presented to the user.
8. If the user so desires, the process may be repeated until the desired outcome is achieved.

The units of assigned priority or weights can be arbitrary, and only their ratio to each other is important. In the system represented by reduction to practice of the present invention, the weights are unitless integers between zero and ten. However a logarithmic scale may also at case, "1" would be the inflection point. Weight values between "0" and "1" downweight priorities while weights greater than "1" upweight priorities.

In this type of system, using a weight vector, w, the Euclidean distance between the two vectors would be computed as:

$$D_{A,B} = \left[\sum_{j=1}^{j=n} w_j(x_{jA} - x_{jB})^2\right]^{\frac{1}{2}} \quad [7]$$

where:
$D_{A,B}$=the distance between vectors A and B; and,
$W_j$=the weight assigned to vector element j.

To illustrate the new computation of the Euclidean distance as influenced by the assigned weights ($w_j$) for the two previous binary dimension 5 vectors: A=1 1 0 1 1 and B=0 1 1 1 0. The calculation of the new Euclidean distance from A to B is as follows:

| A − B = C | | | C * C | Weight | Sum of C | Distance |
|---|---|---|---|---|---|---|
| 1 | 0 | 1 | 1 | 3 | 9 | 3 |
| 1 | 1 | 0 | 0 | 1 | | |
| 0 | 1 | −1 | 1 | 3 | | |
| 1 | 1 | 0 | 0 | 1 | | |
| 1 | 0 | 1 | 1 | 3 | | |

The new weighted Tanimoto Coefficient derived from Equation [2] would be computed according to equation [8]:

$$S_{A,B} = \frac{\sum_{j=1}^{j=n} w_j x_{jA} x_{jB}}{\sum_{j=1}^{j=n} w_j(x_{jA})^2 + \sum_{j=1}^{j=n} w_j(x_{jB})^2 - \sum_{j=1}^{j=n} w_j x_{jA} x_{jB}} \quad [8]$$

Likewise, the new weighted Hamming Distance derived from Equation [3] would be computed using equation [9]:

$$D_{A,B} = \sum_{j=1}^{j=n} w_j |x_{jA} - x_{jB}| \quad [9]$$

The new weighted Soergel distance derived from Equation [4] would be computed using Equation [10]:

$$D_{A,B} = \frac{\sum_{j=1}^{j=n} w_j |x_{jA} - x_{jB}|}{\sum_{j=1}^{j=n} w_j \max(x_{jA} \cdot x_{jB})} \quad [10]$$

The new weighted Dice coefficient derived from Equation [5] would be computed using Equation [11]:

$$S_{A,B} = \frac{2\sum_{j=1}^{j=n} w_j x_{jA} x_{jB}}{\sum_{j=1}^{j=n} w_j(x_{jA})^2 + \sum_{j=1}^{j=n} w_j(x_{jB})^2} \quad [11]$$

and the new weighted Cosine coefficient derived from Equation [6] would be computed using Equation [12]:

$$S_{A,B} = \frac{\sum_{j=1}^{j=n} w_j x_{jA} x_{jB}}{\left[\sum_{j=1}^{j=n} w_j (x_{jA})^2 \sum_{j=1}^{j=n} w_j (x_{jB})^2\right]^{\frac{1}{2}}} \quad [12]$$

Figure 3:
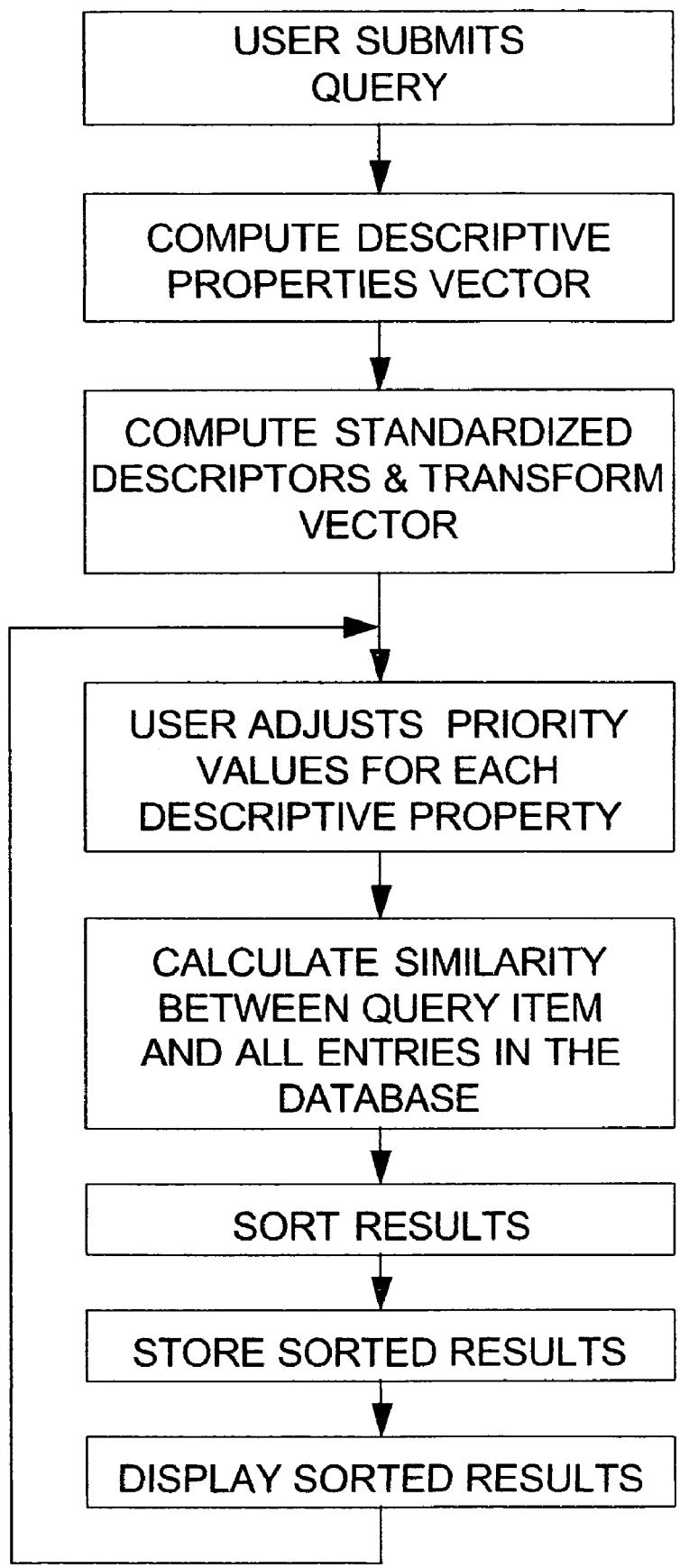
FIG. 3 is an overview program flowchart showing the computerized method of the invention disclosed herein being used to perform similarity searches for a generalized database including the step of standardization.

In many cases, the descriptors will be binary digits—a "one" indicating the presence of a descriptive property and a "zero" indicating its absence. In other cases, the descriptors will have non-binary values. The above indicated method will work effectively in both situations. However, where non-binary descriptive properties comprising the data are used, some of the vector descriptors could be so much larger than others that the search would be biased in favor of the numerically larger descriptors. FIG. 3 shows the program flowchart of FIG. 2 with the step of standardization of the descriptors and vector transformation added to the process. A standardization and vector transformation step is performed as follows:

1. For each descriptor in the database, determine the mean value and standard deviation.
2. Subtract the mean value from each descriptor in both the database vectors and the query vector. The new mean value will now be zero. Some descriptors will be positive and some will be negative.
3. Divide each descriptor by its standard deviation.

Other standardization techniques well known in the statistical arts may also be used.

As previously mentioned, one of the preferred uses for this methodology implemented as a computerized system is as a means to selectively search a database of chemical compounds. Representations of chemical compounds can be decomposed into chemical structure fragments. During product development of organic compounds, it is often important to search for other compounds having a similar molecular structure in an effort to adjust the new structure so as to improve its chemical, biological, and physical properties. Such a search is also necessary to insure that the new product does not infringe on patented products previously developed by others.

Computerized searching of organic chemical compound databases has been around for decades. Many of these databases store molecular information according to chemical structure fragments. The data processing systems maintain a fragment dictionary, and all compounds input into the database are parsed so as to establish a relationship between fragments in the dictionary. The dictionary is instituted with fragments well known to those skilled in the art. Many database searching tools use fragment dictionaries with a large number of entries, and others use fragment dictionaries with a smaller number of entries.

One possible representation of a complex molecule would be to parse it into a binary fragment vector. Each bit represents the presence of absence of a particular fragment in the dictionary. The vector element order is keyed to the fragment dictionary. Fragments from a fragment dictionary or fragments generated by an algorithm are used for substructure searches of the molecule. When a match is found, the element for molecular descriptor vector corresponding to the matched fragment is set to 1. The binary vector may be represented logically as a string of bits or bytes or may have any convenient representation. These binary vectors then form a fingerprint for the chemical structure of the molecule. Each bit or fragment in the fingerprint is a dimension representing one row in the vector.

Searching using a fragment dictionary is commonly used in chemical database technology. Chemical Abstracts (CAS/STN) uses a dictionary of two-thousand fragment keys in the dictionary for a database of approximately ten-million chemical compounds. Most commercial databases use a dictionary of between five-hundred to one-thousand keys for a database of approximately one-million to two-million chemical compounds. The inventors have reduced the current system to practice. Said system uses a dictionary 230 fragment keys for a database of approximately seventy-thousand compounds. The performance of said system is excellent.

In addition to chemical structure fragment descriptors, other chemical descriptors may be usefully included in the description of a compound. Properties such as pKa, LogP, MR, IR, hydrogen bond donor count, hydrogen bond acceptor count, heteroatom count, molecular weight, Rule of 5 value (Lipinski value), retention value, or spectroscopic peak measurements may be used to characterize the properties of compounds. These descriptors can be included in compound fingerprints and used in both chemical and biological similarity calculations.

Figure 4:
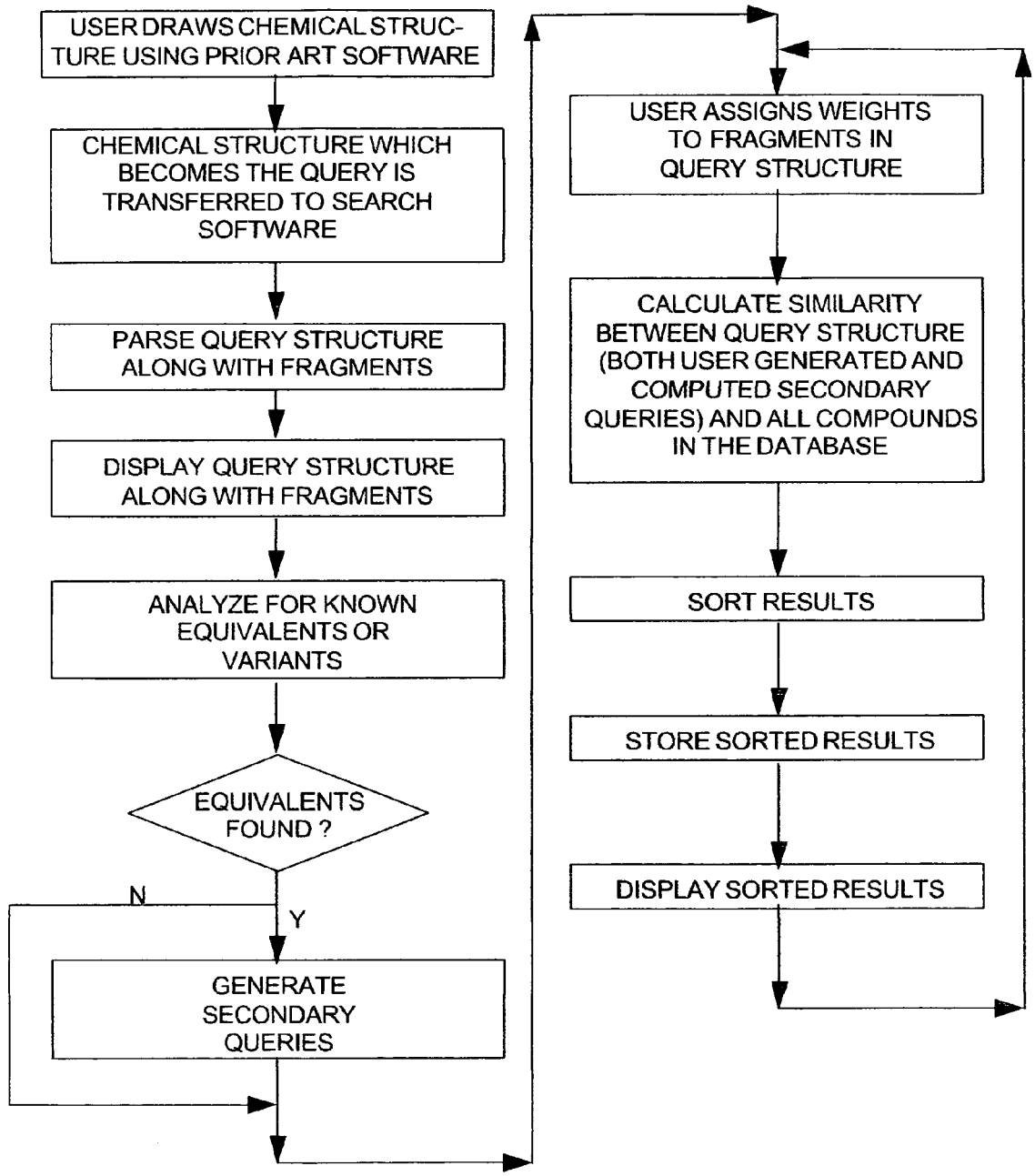
FIG. 4 is an overview program flowchart showing the computerized method of the invention disclosed herein being used to perform similarity searches in a database of organic chemical compounds.

FIG. 4 is an overview program flowchart showing the computerized method of the invention disclosed herein being used to perform similarity searches in a database of organic chemical compounds. In designing a search query system for a chemical compound database, the following steps must be performed:

1. Draw the query:—A user draws a chemical structure using a chemical structure drawing package such as ChemDraw, ISISDraw, or CASDraw. The resulting chemical structure, the query structure, is transferred to the program implementing the search.
2. Fingerprint the query:—Use the dictionary of chemical structure fragments or an algorithm that generates the fragments to characterize the chemical structure. The searching program determines which structure fragments, from the fragment dictionary or algorithm, are present in the query structure.
3. Search query for substructure equivalents:—Search the query structure for defined equivalents, such as heterocycles or bio-isosteres. If the equivalents are present, copies of the query are made and edited to generate related molecules. Similarity search will be performed on the query and the related equivalent structures.
4. Allow the user to adjust the fragment weighting:—An electronic form displaying the structure fragments, from the fragment dictionary, which are present in the query structure is displayed to the user. For each structure fragment, there is also present a control that allows the user to define the importance of the fragment. The control on the form could be a slider with a numeric scale, a dial with a numeric scale, a text box allowing numeric value entry, or any graphic or text based system that would permit the user to interactively assign a weight to the importance of a particular structure fragment. Alternatively, the fragment weights may be input from a file.
5. Run the similarity search:—After the user has assigned the structure fragment weights, the similarity search is performed using a Euclidean distance, the Tanimoto coefficient, or other method of comparing the similarity between two vectors.

6. Return Results:—The results of the similarity search may be stored for future use. The results are then displayed to the user. In the preferred embodiment, they would be shown as a graphical series of compounds sorted in order of decreasing importance. However, any method of user informative display could be used.

Figure 5:
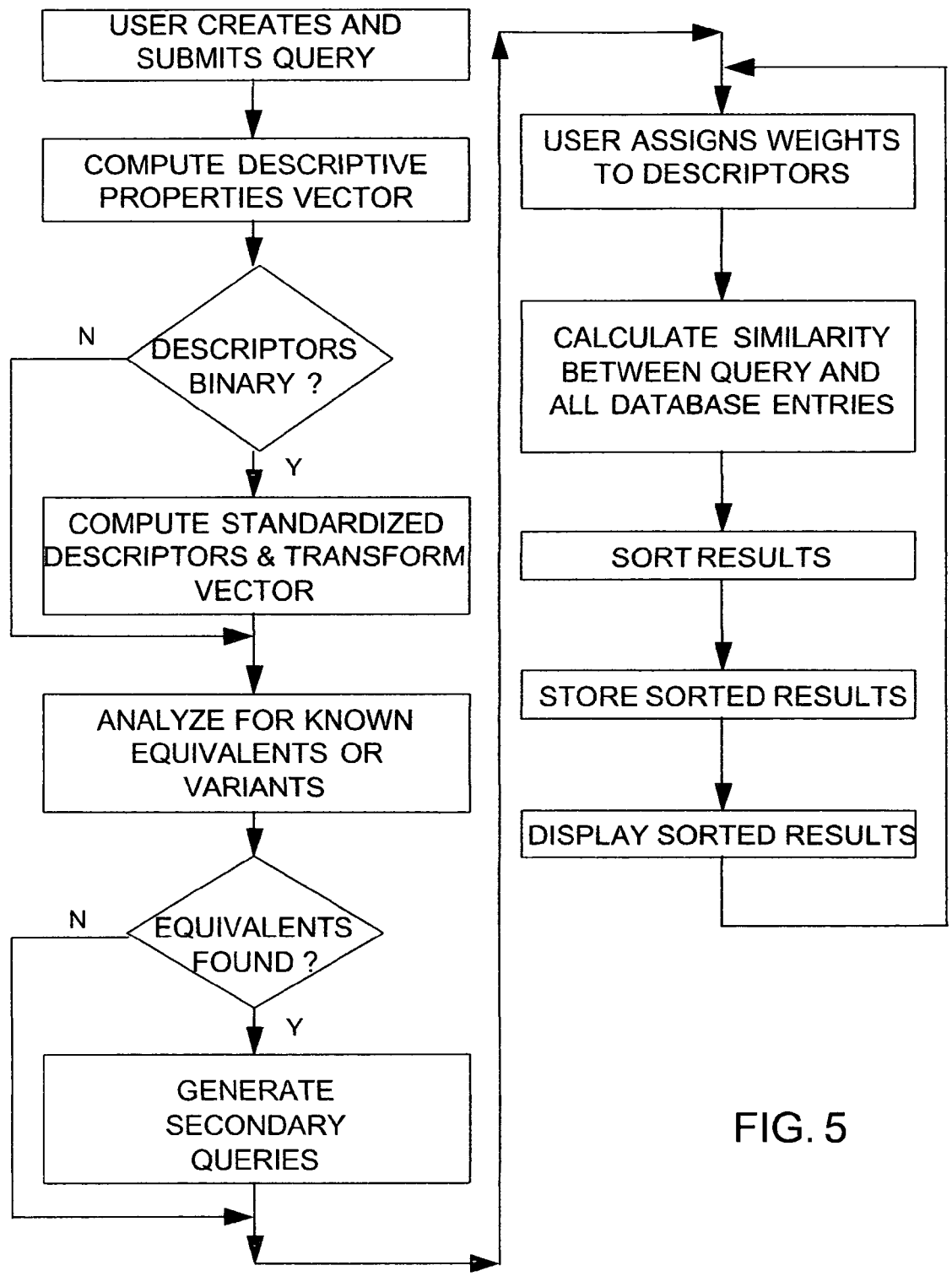
FIG. 5 is an overview program flowchart showing the computerized method of the invention disclosed herein being used to perform similarity searches in a database of organic chemical compounds including the step of standardization.

FIG. 5 is a program flowchart showing the computerized method of the invention disclosed herein being used to perform similarity searches in a database of organic chemical compounds including the step of standardization. This flowchart also illustrates a generalized method of searching a computer database that includes the step of standardization (i.e., where the descriptors are non-binary numbers) and the step of creating secondary queries (i.e., where equivalents or variants of the descriptors are known and included in the database).

Figure 6:
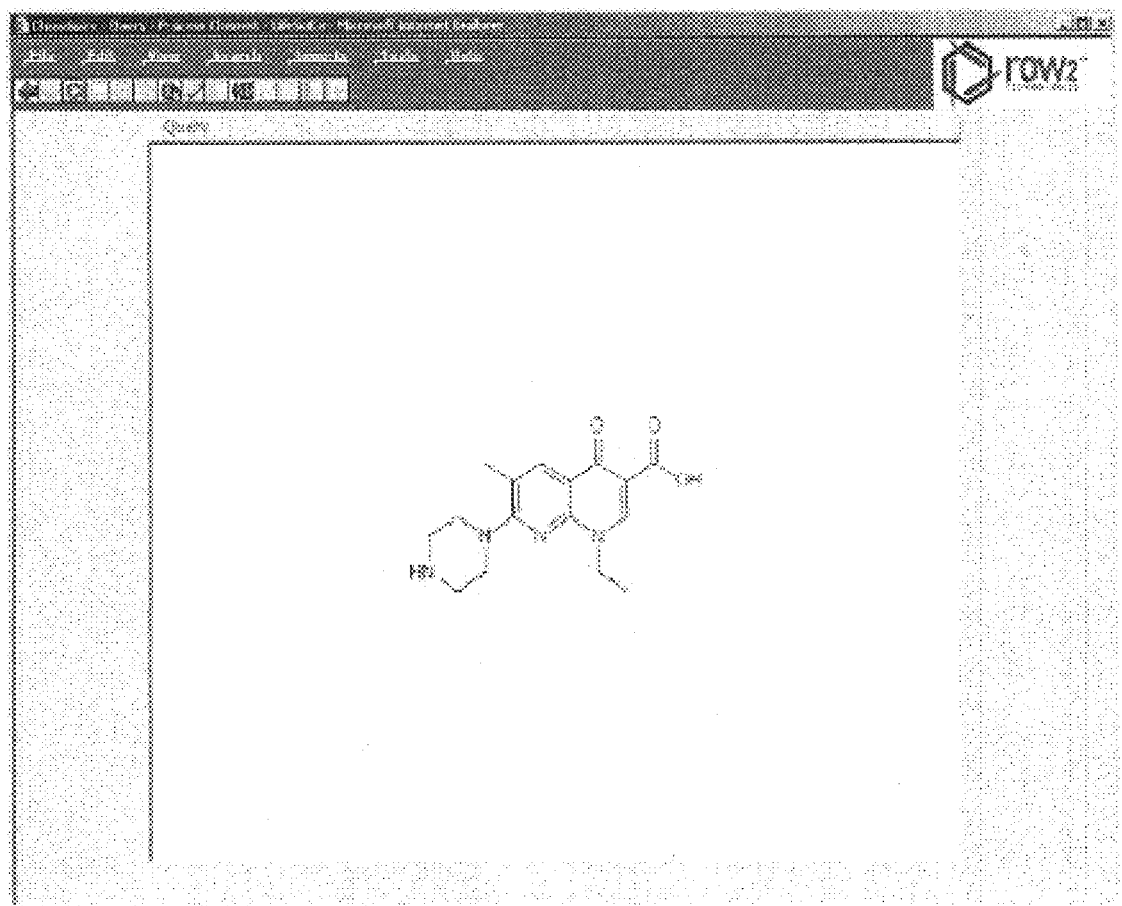
FIG. 6 shows the screen view of the chemical structure of the query compound, Trovafloxacin, as drawn by the user with one of the standard chemical drawing software packages and input into the search program.

Using the above method of searching, the search may be biased in a direction defined by the user. The above tunable search process applied to organic chemical compounds is illustrated in FIG. 6 through FIG. 9. FIG. 6 illustrates a computer monitor screen display of the chemical structure of query compound

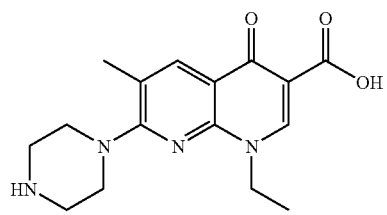

Figure 7:
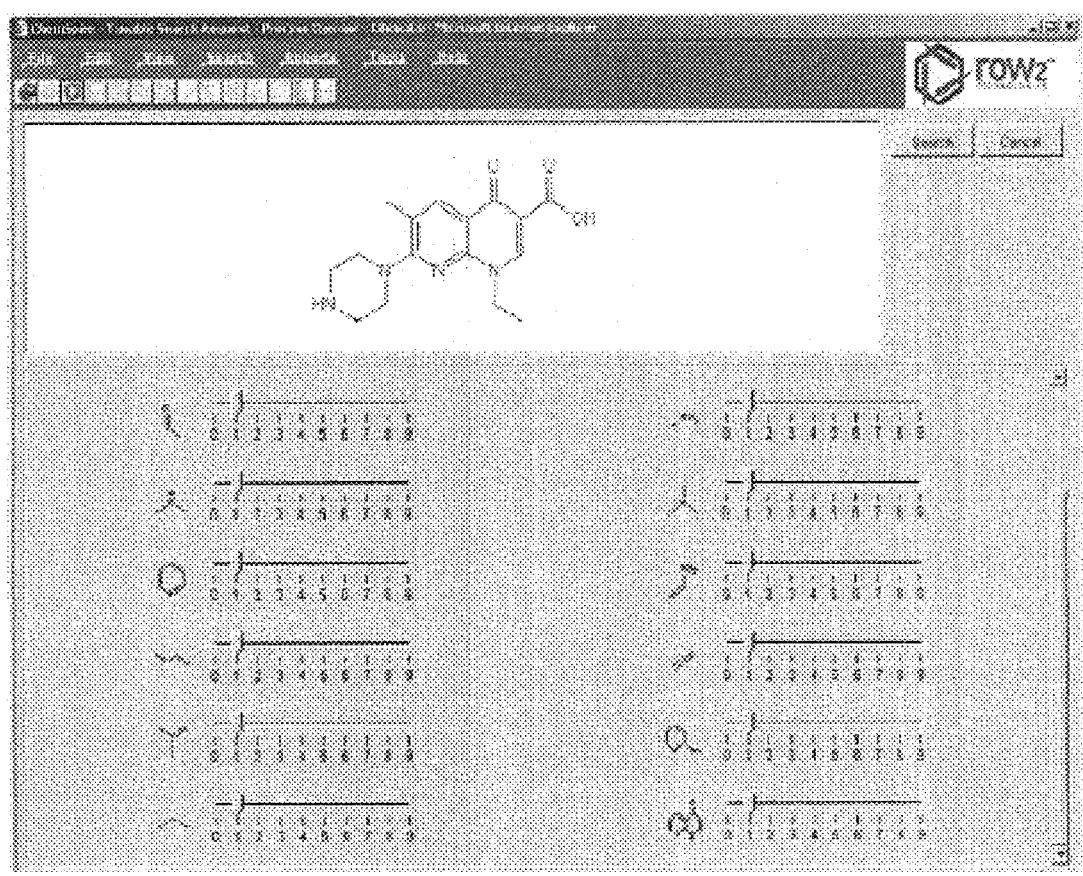
FIG. 7 shows the structure of the query compound having been parsed or fingerprinted according to chemical structure fragments in a fragment dictionary. Only twelve fragments are shown on the screen in the figure. However, a slider on the right edge of the screen may be used to display additional fragments. An adjustable slider with a numeric scale is associated with each fragment shown.

Trovafloxacin ($C_{20}H_{15}F_3N_4O_3$) as input through one of the standard chemical drawing packages. FIG. 7 shows the structure of the query compound having been "fingerprinted" using the twelve fragments

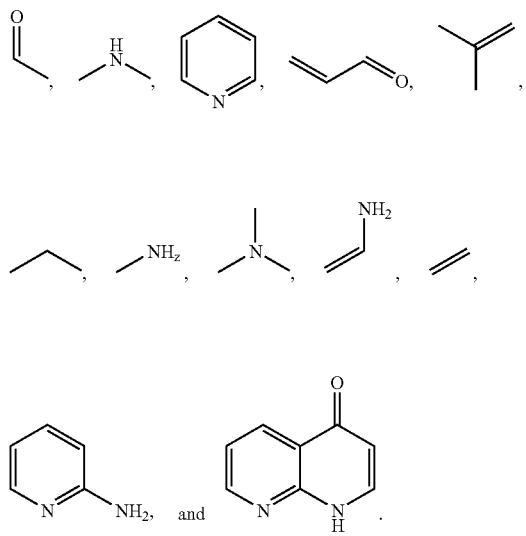

Figure 8:
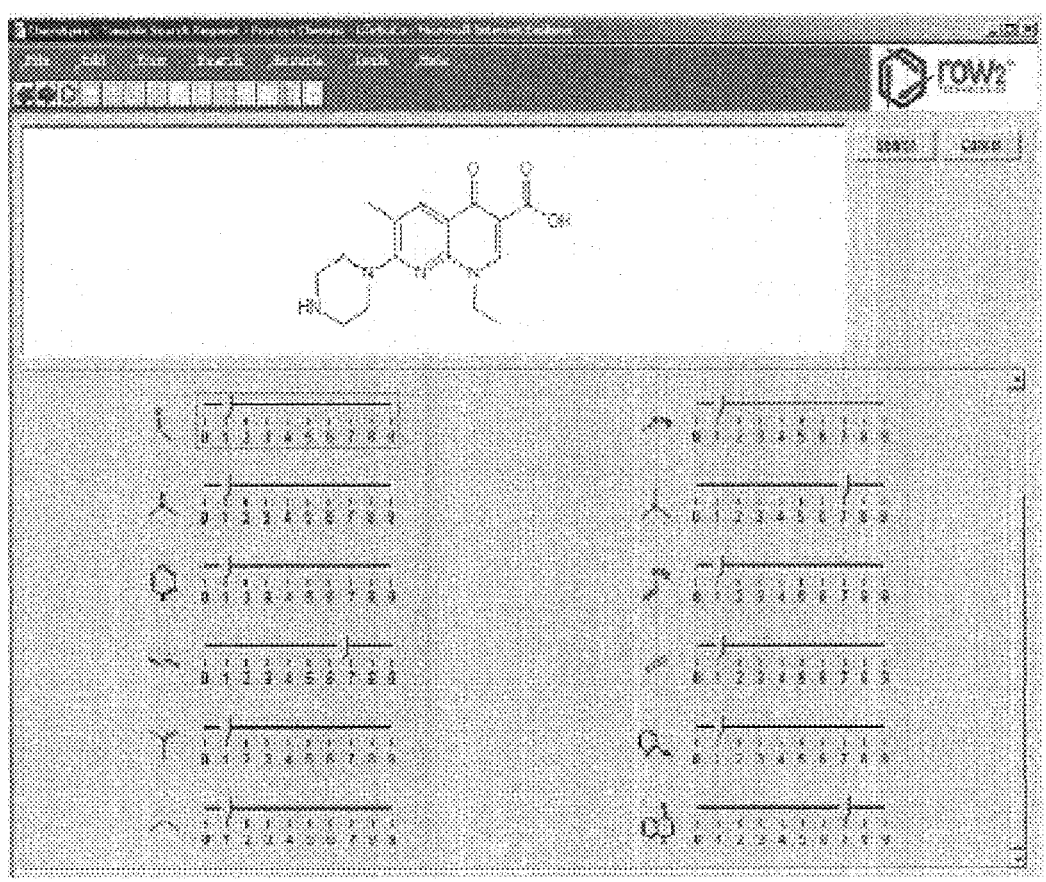
FIG. 8 is the screen of FIG. 7 after the user adjusted some of the sliders so as to assign weights to their associated fragments.

These are shown graphically on the lower portion of the screen. Sliders are shown next to each fragment all preset to their default values of 1. FIG. 8 shows the same screen where the user has set the sliders for the

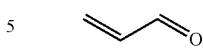

fragment to 6.5, the

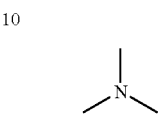

fragment to 7, and the

Figure 9:
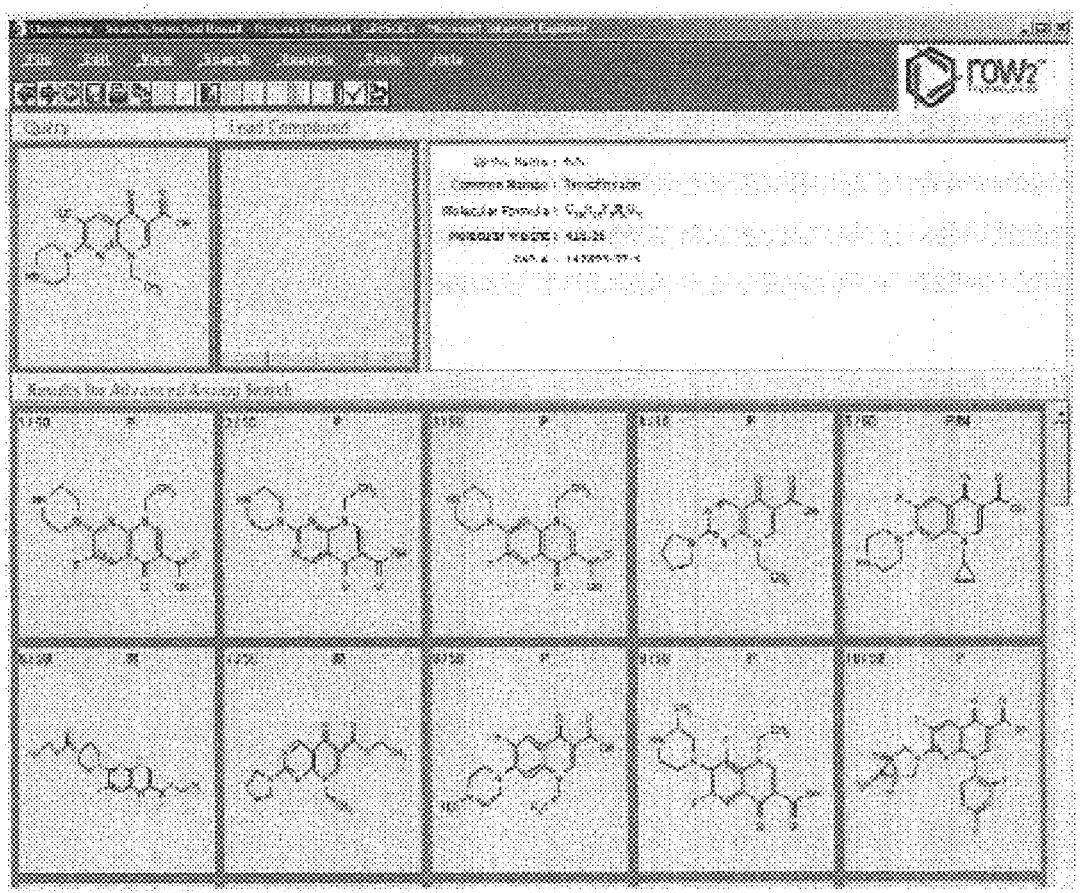
FIG. 9 shows the results of the similarity search for the query compound with compounds in the database. The figure shows ten out of fifty compounds returned as part of the search.

to 7. FIG. 9 shows the results of the similarity search. In the figure the first ten compounds (of fifty) found to be similar to Trovafloxacin are shown arranged in order decreasing similarity. For example, the molecule of compound labeled 1/50 is deemed by the search criteria to be most similar. It differs only by substitution of fluorine (F) for the ethyl ($CH_2$) grouping.

Figure 10:
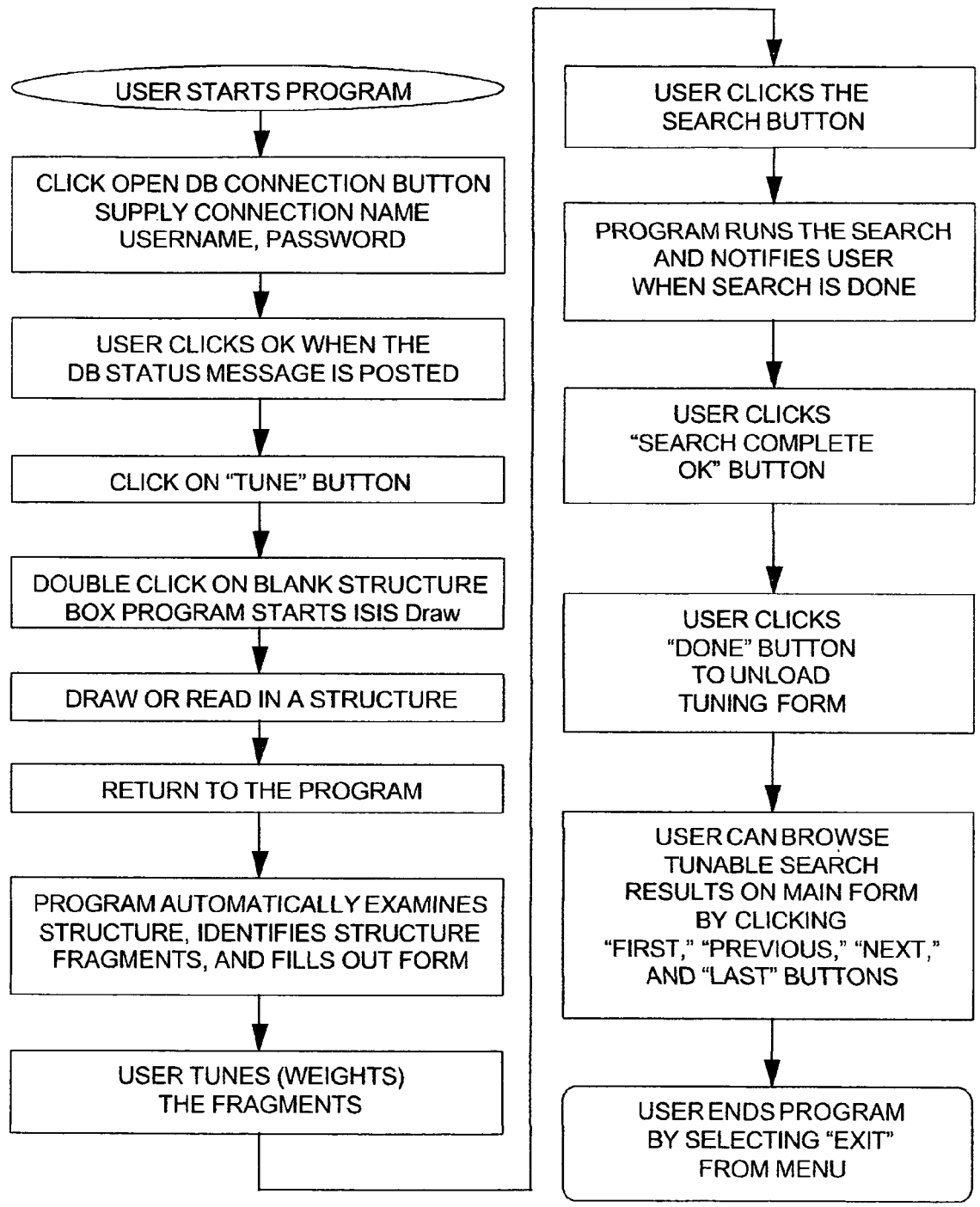
FIG. 10 shows a program flow chart for a specific implementation of the program in FIG. 3 in which the screens shown in FIG. 6 through FIG. 9 are used.

FIG. 10 shows a program flow chart for a specific implementation of the program in shown in FIG. 4 in which the screens shown in FIG. 6 through FIG. 9 are used. A printed program listing for this system can be found in the APPENDIX of U.S. patent application Ser. No. 10/448,168 filed May 28, 2003, said application being incorporated by reference herein in its entirety thereto.

The above mentioned method may also be used to search biological data. A biological response is a continuous variable. For example, the binding strength of a drug to a particular receptor would have a specific numeric value, and it would be important to express that value in the vector. However, the priority or weight that a user would apply to a characteristic such as binding strength for a particular receptor when performing a similarity search is independent of the actual data. Compounds can be described based upon biological response. Plotting the biological response over a series of tests produces a graph possessing a characteristic shape, a biological activity fingerprint. A database compounds and biological test results may be probed for those having characteristic biological activity fingerprints. Compounds having similar fingerprints often have similar modes of action. In this case, standardization of the descriptors could be used to eliminate search biasing due to large numeric variations in different descriptors.

In addition to chemical structure fragment descriptors, other chemical descriptors may be usefully included in the description of a compound. Properties such as pKa, LogP, MR, IR, hydrogen bond donor count, hydrogen bond acceptor count, heteroatom count, molecular weight, Rule of 5 value (Lipinski value), retention value, or spectroscopic peak measurements may be used to characterize the properties of compounds. These descriptors can be included in compound fingerprints and used in both chemical and biological similarity calculations.

Figure 11:
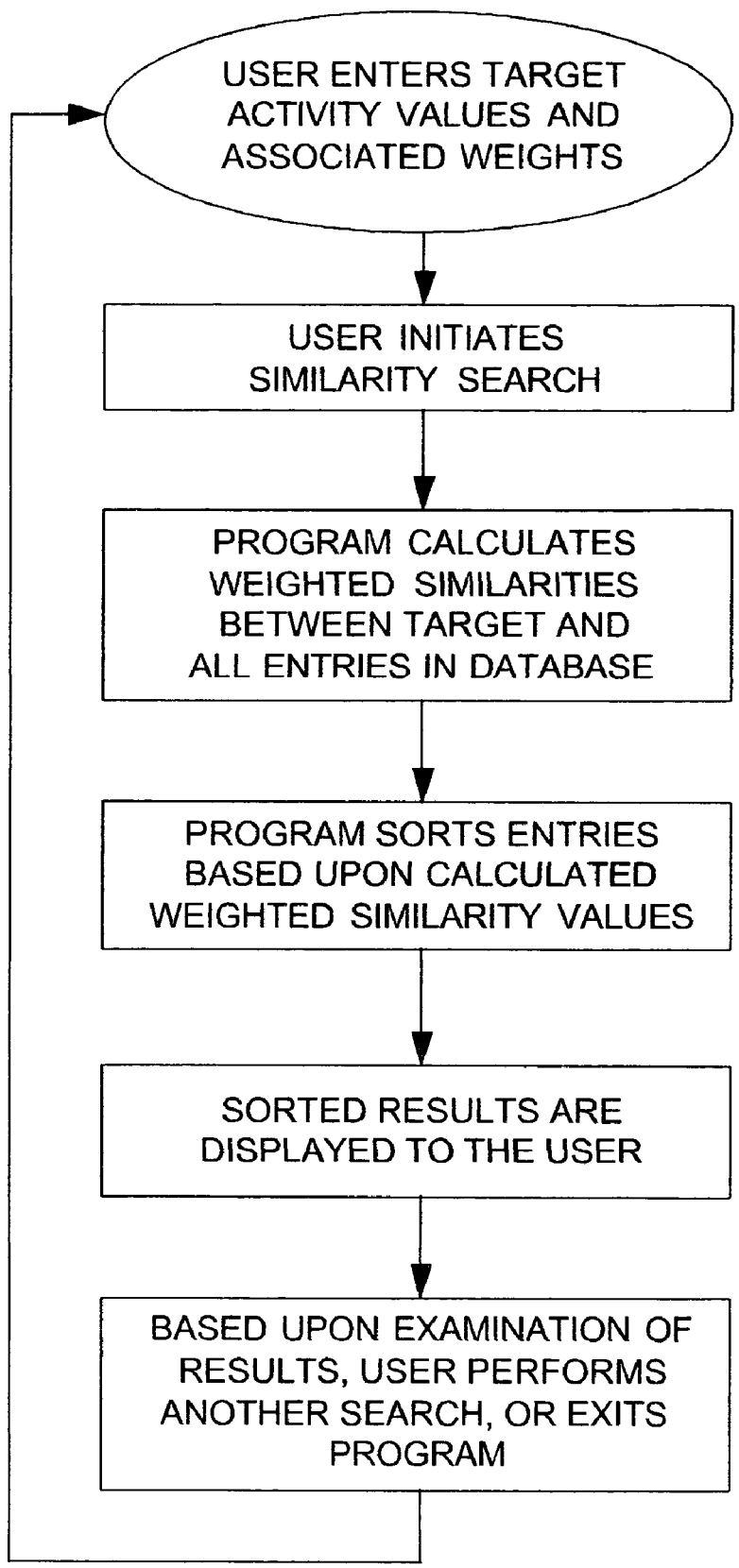
FIG. 11 is an overview program flowchart showing the computerized method of the invention disclosed herein being used to perform similarity searches in a database of biological responses to various compounds.

FIG. 11 is an overview program flowchart showing the computerized method of the invention disclosed herein being used to perform similarity searches in a database of biological responses to various compounds. The implementation of the method described herein is in the form of a MICROSOFT EXCEL Spreadsheet with macros performing all of the necessary functions. A source code listing for this implementation appears in a section entitled, "COMPUTER PROGRAM LISTING—TUNABLE BIOLOGICAL SEARCH," at the end of U.S. patent application Ser. No. 10/448,168. The data shown in the spreadsheet of FIG. 12 has been separated into three parts, viz., FIG. 12(a), (b), and (c). The source of the data (hereinafter the LEWI Data) is the paper: Janssen, Paul A. J.; Niemegeers, Carlos J. E.; and Schellekens, Karel H. L.; "Is it Possible to Predict the Clinical Effects of Neuroleptic Drugs (Major Tranquillizers) from Animal Data?—Part I: 'Neuroleptic activity spectra' for rats"; from the Janssen Pharmaceutic n.v., Research Laboratoria, Beerse (Belgium), *Drug Research*, Vol 15, *Heft* 2, 1965, pp 104–117. A copy of this paper was provided with U.S. patent application Ser. No. 10/448,168, and is incorporated by reference as non-essential material in its entirety herein.

The following features are needed:
1. A row of target biological activity scores to use as a target in the similarity search. In the LEWI Data, there are twelve measured responses.
2. A row of weighting values to apply to the target biological responses. Weightings are input by the user to indicate the relative importance that the user places on the importance of the associated biological test.
3. A collection of data related to individual compounds and their associated biological responses. For the purposes of this implementation, the data are contained within the same spreadsheet as the target input scores and the target weightings. The LEWI Data set contains data on 40 compounds.

The program works as follows:
1. After the user has entered the biological response values, and the associated biological response weightings, the user initiates the calculation by pressing the button for Euclidean Distance or Tanimoto Coefficient.
2. Using the user-supplied biological activity target values, and user-supplied target weightings, the similarity values are calculated for each compound in the data set.
3. The calculated similarity values for each compound in the data set is stored.
4. After the similarity values for all the compounds in the data set have been calculated, the data is then sorted in order of decreasing similarity.

For the convenience of the user, other features have been added:
To simplify the entry of target biological activity values, a control box has been set up to allow the user to select a compound from the data set to use as a starting point data entry. Biological activity values from a selected data set compound are loaded. Then the user can modify the values to suit his or her needs.
When scrolling through the sorted output data, a graph showing the relationship between the input target and the data set compound data currently selected can be shown.

Figure 12A:
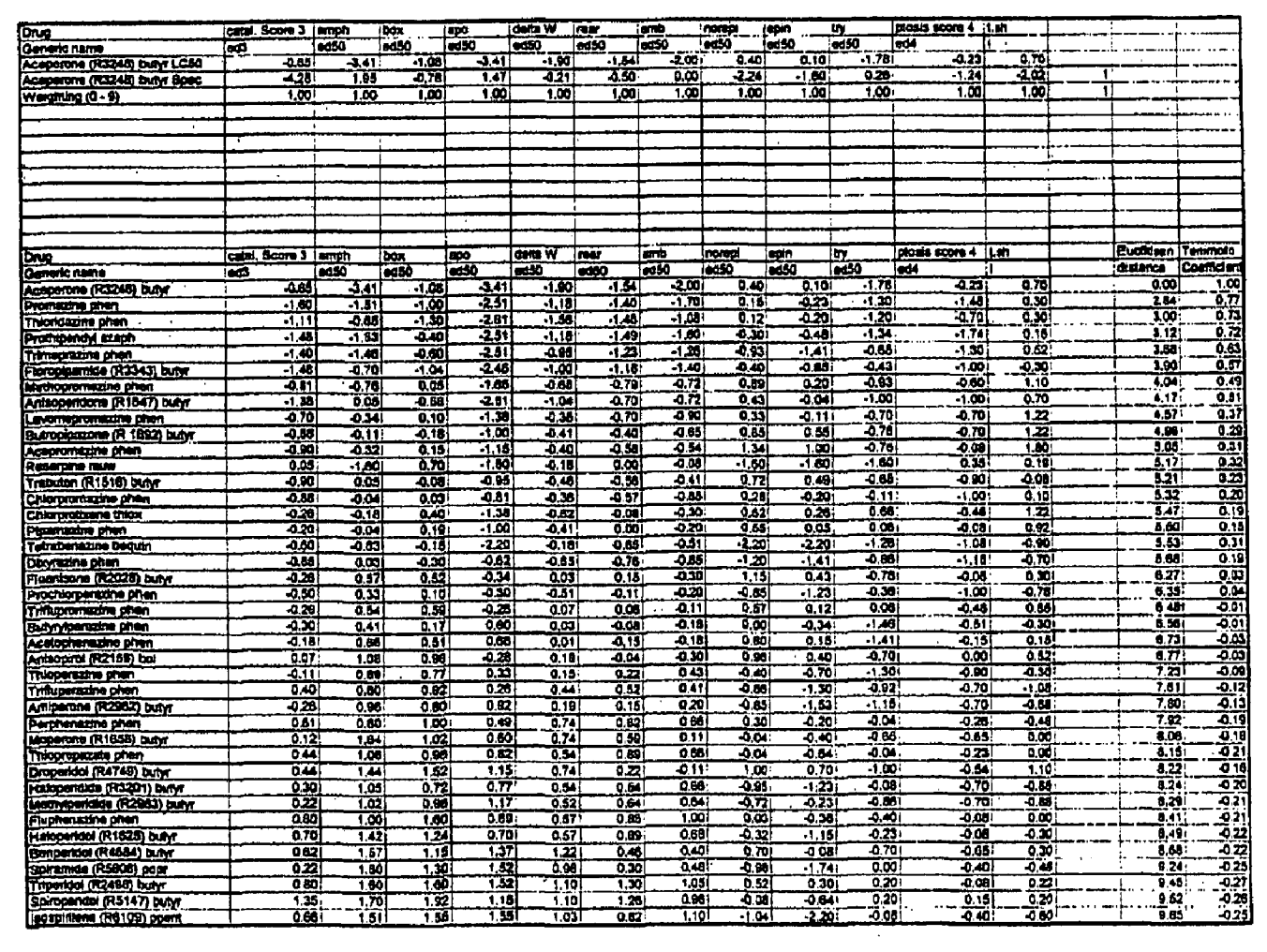
Figure 12B:
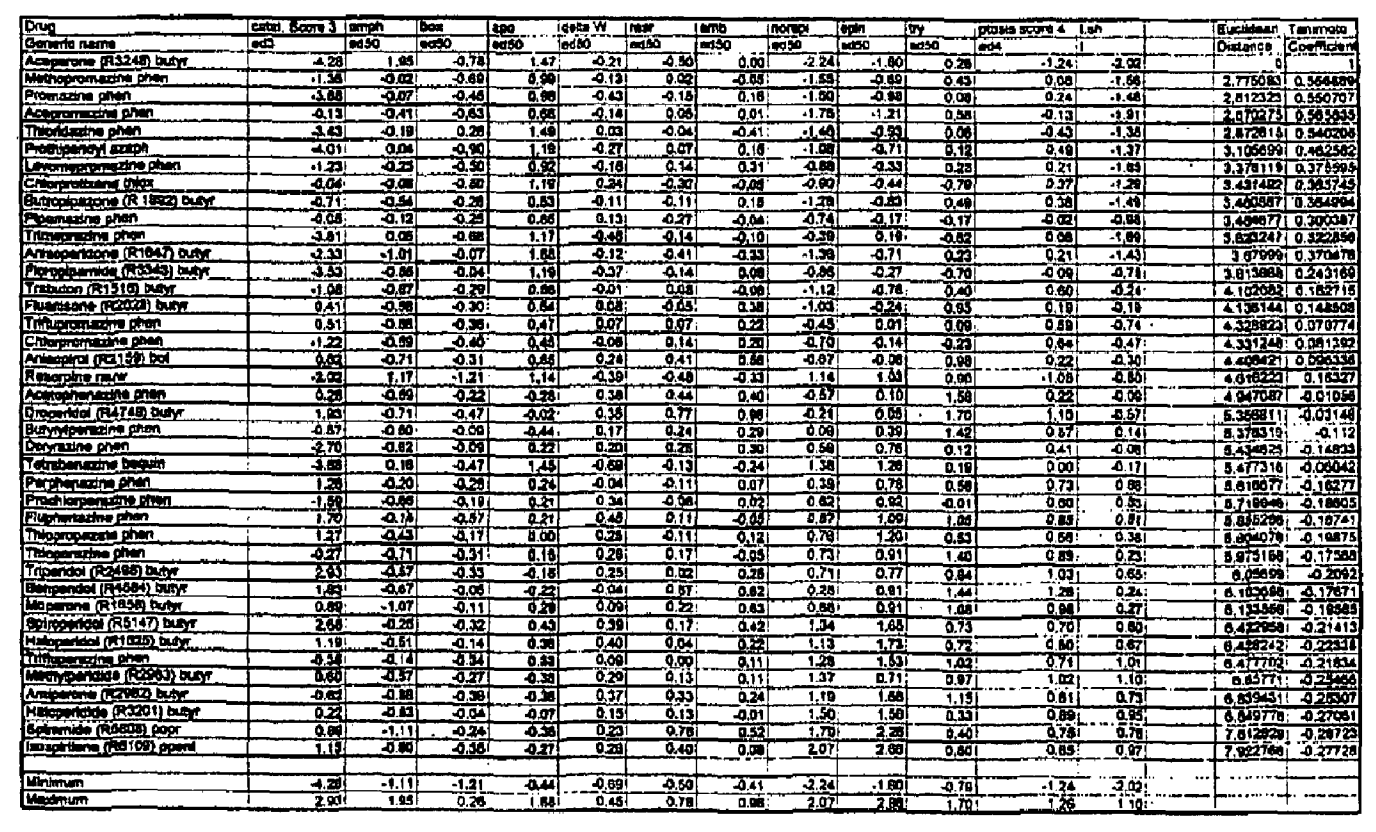

FIG. 13 represents four screen prints of the program shown in FIG. 9 operating on the data shown in FIG. 12. The figure is divided into four parts, viz., FIG. 13(a), (b), (c), and (d). The data for all versions of FIG. 13 are those shown in FIG. 12(a).

Figure 13A:
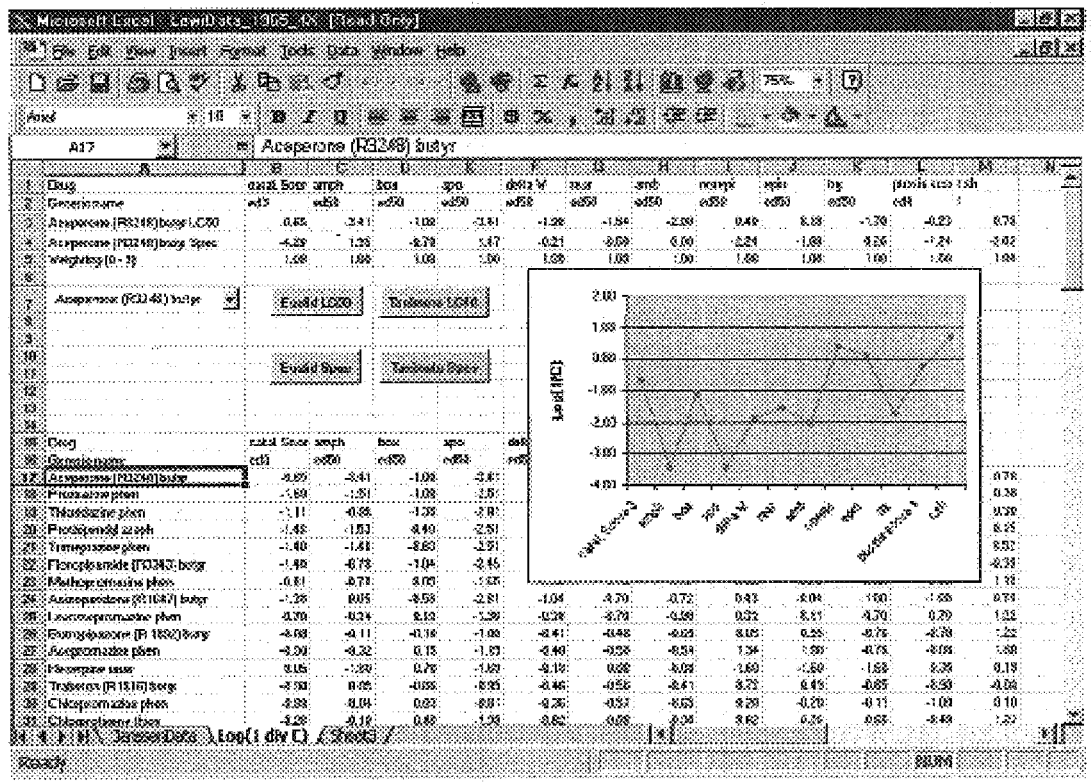
FIG. 13 represents four screen prints of the program shown in FIG. 11 operating on the data shown in FIG. 12.

In FIG. 13(a), the cursor is positioned on the Target compound, Aceperone (R3248) butyr (Row 17-Column A). The chart shows the Tanimoto fingerprint for twelve test results on rats on a logarithmic scale. Note the "Euclid LC50" and "Tanimoto LC50" radio buttons. Since the target compound is only being compared with itself, only one fingerprint is shown.

Figure 13B:
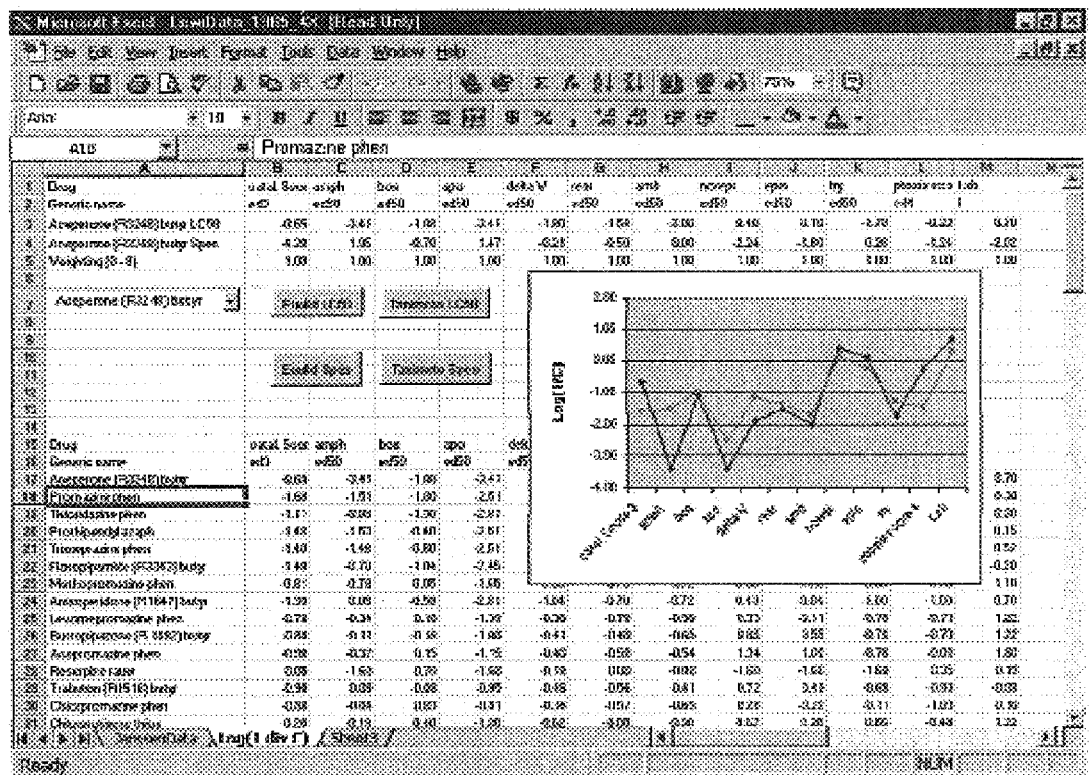

In FIG. 13(b), the cursor is positioned on Promazine phen (Row 18-Column A). Here, the chart compares two fingerprints. The darker graph is the fingerprint of Aceperone (R3248) butyr while the lighter graph is the fingerprint of Promazine phen. Note how closely the fingerprints of these adjacently sorted compounds resemble each other.

Figure 13C:
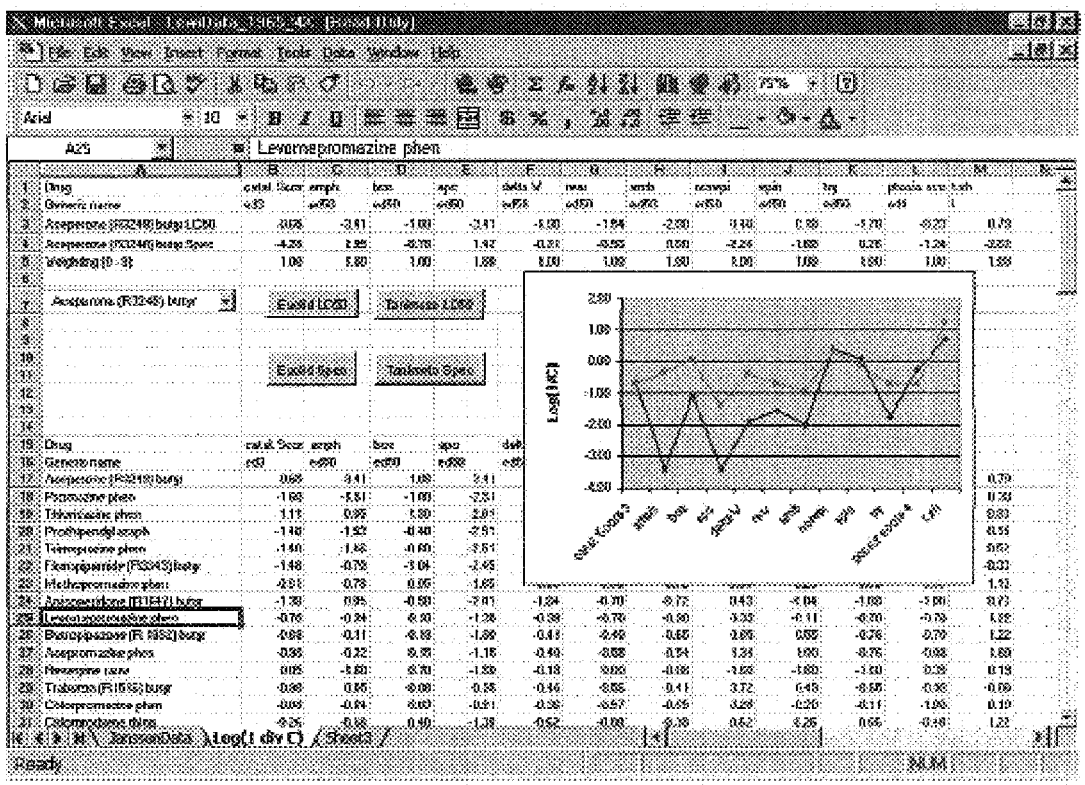

In FIG. 13(c), the cursor is positioned on Levomepromazine phen (Row 25-Column A). Once again there are two fingerprints being compared where the darker graph is the fingerprint of Aceperone (R3248) butyr and the lighter graph is the fingerprint of Levomepromazine phen. Note here that the two graphs are far less similar than those of FIG. 13(b).

Figure 13D:
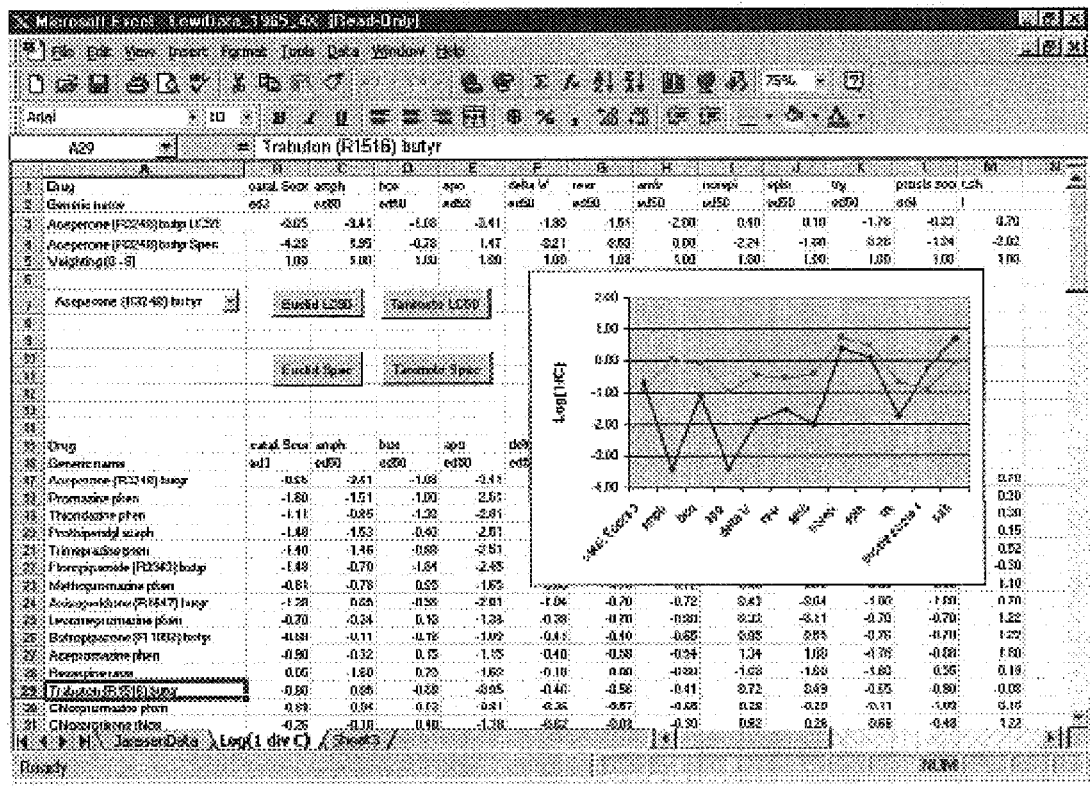

In FIG. 13(d), the cursor is positioned on Trabuton (R1516) butyr (Row 29-Column A). The darker graph is the fingerprint of Aceperone (R3248) butyr and the lighter graph is the fingerprint of Trabuton (R1516) butyr. Here, the two fingerprint graphs are far less similar than those of FIGS. 13(b) and (c).

The systems, methods, and programs disclosed herein may be implemented in hardware or software, or a combination of both. Preferably, the techniques are implemented in computer programs executing on programmable computers that each comprise a processor, a storage medium readable by said processor (including volatile and non-volatile memory and/or storage elements), at least one input device, and at least one output device. The programs may be implemented allowing user communication via a network connection using a modem or LAN or WAN or wireless network or other communication network. Program code is applied to data entered using the input device to perform the functions described and to generate output information. The output information is routed to one or more output devices.

Each such computer program is preferably stored on a storage medium or device (e.g., CD-ROM, hard disk, magnetic tape, or magnetic diskette) that is readable by a general or special purpose programmable computer. Said computer program configures and operates the computer when the storage medium or device is read by the computer to perform the procedures described in this application. The system may also be considered to be implemented as a computer-readable storage medium, configured with a computer program, where the storage medium so configured causes a computer to operate in a specific and predefined manner. The present invention may be embodied in computer-readable media, such as floppy disks, ZIP or JAZ disks, conventional hard disks, optical media, CD-ROMS, Flash ROMS, nonvolatile ROM, RAM and any other equivalent computer memory device. It will be appreciated that the system, method of operation and product may vary as to the details of its configuration and operation without departing from the basic concepts disclosed herein.

Some or all of the functionality may be implemented on an analog computer or device or on a hybrid digital/analog computer. User tuning (i.e., the process whereby weights are assigned to the specific descriptive properties) is an area of the computerized process most applicable to analog processing. The analog processing devices used may be inter alia electrical, mechanical, optical, hydraulic, or any other means for analog processing. Analog-to-digital or digital-to-analog conversion may take place at any step of the process.

Based upon the disclosure of the systems, processes, methods, and computer programs herein, as well as the foregoing discussion of apparatus considerations, it is apparent that one skilled in the art would be able to implement the present invention on any of the apparatuses or devices mentioned above without undue experimentation.

We claim:

1. A method for comparing entries with characteristics in an electronic database, wherein the characteristics are capable of being represented by numeric descriptors, said method comprising:

assigning to each entry a numeric entry vector, the elements of which comprise descriptors that represent the characteristics in a predetermined order;

establishing a query to be compared with the entries;

assigning to the query, an original numeric query vector, the elements of which comprise descriptors that represent the characteristics in the predetermined order;

specifying, for each element of the original query vector, a numeric weight representing the relative importance of that characteristic to the other characteristics;

constructing a weight vector, each element of which is populated with the specified numeric weight that is representative of the characteristic represented in the corresponding element of the original query vector;

calculating for each entry in the database a weighted similarity value using the original query vector, the entry vector, and the weight vector;

ordering the entries according to their similarity values; and, displaying the ordered entries.

2. The method of claim 1 further comprising analyzing the query for the presence of characteristics having defined equivalents or variants, and if such equivalents or variants are found:

creating a set of numeric query vectors, consisting of one vector for each equivalent or variant, the elements of which comprise descriptors that represent the characteristics in the predetermined order, wherein descriptors that represent the equivalents or variants are substituted for their respective descriptors in the original query vector;

calculating for each entry in the database a weighted similarity value using each vector of the set of query vectors, the entry vector, and the weight vector; and, merging and ordering the entries according to the similarity values calculated using the original query vector and the set of query vectors.

3. The method of claim 1 further comprising standardizing the original query vector and all of the entry vectors.

4. The method of claim 3 wherein standardizing comprises:

calculating a mean value and standard deviation for each descriptor of all the entry vectors;

forming new entry vectors for each entry in the database by subtracting the mean value from its respective descriptor in each entry vector;

forming an adjusted query vector by subtracting the mean value from its respective descriptor in the original query vector; and, dividing each descriptor in each new entry vector and in the adjusted query vector by its standard deviation.

5. The method of claim 2 further comprising standardizing all of the entry vectors and all of the vectors of the set of query vectors.

6. The method of claim 5 wherein standardizing comprises:

calculating a mean value and standard deviation for each descriptor of all the entry vectors;

forming new entry vectors for each entry in the database by subtracting the mean value from its respective descriptor in each entry vector;

forming a supplemental set of query vectors by subtracting the mean value from its respective descriptor in each vector of the set of query vectors; and, dividing each descriptor in each new entry vector and in each vector of the supplemental set of query vectors by its standard deviation.

7. The method of claim 1, 2, 3, or 5 wherein the numeric weights can be assigned by a user.

8. The method of claim 7 wherein the user can assign the numeric weights by manipulating objects on a computer screen.

9. The method of claim 8 wherein said objects comprise sliders with numeric scales.

10. The method of claim 8 wherein said objects comprise dials with numeric scales.

11. The method of claim 8 wherein said objects comprise text boxes allowing numeric entry.

12. The method of claim 7 wherein, following display of the ordered entries, said method further comprises:

re-specifying, for each descriptor of any of the query vectors, a new numeric weight representing a refined relative importance of that characteristic to the other characteristics;

constructing a new weight vector, the elements of which are populated with the new weights which are representative of the descriptors in the predetermined order;

re-calculating for each entry new similarity values using each query vector;

re-ordering the entries according to their new similarity values;

displaying the re-ordered entries; and, repeating the above actions as often as desired by the user.

13. The method of claim 1, 2, 3, or 5 wherein said similarity value is calculated using a weighted Euclidean Distance between any query vector and any entry vector.

14. The method of claim 1, 2, 3, or 5 wherein said similarity value is calculated using a weighted Hamming Distance between any query vector and any entry vector.

15. The method of claim 1, 2, 3, or 5 wherein said similarity value is calculated using a weighted Sorgel Distance between any query vector and any entry vector.

16. The method of claim 1, 2, 3, or 5 wherein said similarity value is calculated using a weighted Tanimoto Coefficient between any query vector and any entry vector.

17. The method of claim 1, 2, 3, or 5 wherein said similarity value is calculated using a weighted Dice Coefficient between any query vector and any entry vector.

18. The method of claim 1, 2, 3, or 5 wherein said similarity value is calculated using a weighted Cosine Coefficient between any query vector and any entry vector.

19. The method of claim 1, 2, 3, or 5 wherein each element of each query vector and of each entry vector is either one or zero thereby forming binary vectors.

20. The method of claim 1, 2, 3, or 5 wherein said database entries and said query are representative of structures of chemical compounds.

21. The method of claim 20 wherein said query is generated by a chemical structure drawing package.

22. The method of claim 20 wherein the characteristics of the query and the database entries are characterized by structure fragments.

23. The method of claim 22 wherein any query vector and all entry vectors are binary vectors indicating the presence or absence of said structure fragments.

24. The method of claim 22 wherein the structure fragments are contained within and referenced in an electronic dictionary.

25. The method of claim 22 wherein the structure fragments are generated automatically.

26. The method of claim 1, 2, 3, or 5 wherein the characteristics associated with said database entries are representative of biological activity screening results and wherein the characteristics associated with said query are also representative of biological activity screening results.

27. The method of claim 1, 2, 3, or 5 further comprising storing a representation of the ordering for further use.

28. A system for searching data comprising:
a database component operative to maintain an electronic database of data,
wherein said data has associated with them a set of one or more entries having characteristics; and,
wherein said characteristics are capable of being represented by numeric descriptors;
a first computation component operative to assign to each entry a numeric entry vector, the elements of which comprise descriptors that represent the characteristics in a predetermined order;
a first input component operative to accept a query datum submitted electronically;
a second computation component operative to assign to the query datum an original numeric query vector, the elements of which comprise descriptors that represent the characteristics in the predetermined order;
a second input component operative to accept numeric weights for each element in the original query vector;
a third computation component operative to construct a weight vector, each element of which is populated with the specified numeric weight that is representative of the characteristic represented in the corresponding element of the original query vector;
a fourth computation component operative to calculate for each entry in the database a similarity value using the original query vector, entry vector, and the weight vector;
a fifth computation component operative to order the entries according to their similarity values; and
a display component operative to display the ordered entries.

29. The system of claim 28 further comprising:
a sixth computation component operative to analyze the query for the presence of characteristics having defined equivalents or variants, and if such equivalents or variants are found:
a seventh computation component operative to create a set of query vectors, consisting of one vector for each equivalent or variant, the elements of which comprise descriptors that represent the characteristics in the predetermined order, wherein descriptors that represent the equivalents or variants are substituted for their respective descriptors in the original query vector;
an eighth computation component operative to calculate for each query in the database, a weighted similarity value using each vector of the set of query vectors, the entry vector, and the weight vector; and,
a ninth computation component operative to merge and order the entries according to the similarity values calculated using the original query vector and the set of query vectors.

30. The system of claim 28 further comprising computation components operative to standardize the original query vector and all of the entry vectors.

31. The system of claim 30 wherein the computation components operative to standardize further comprise:
a sixth computation component operative to calculate a mean value and standard deviation for each descriptor of all the entry vectors;
an seventh computation component operative to form new entry vectors for each entry in the database by subtracting the mean value from its respective descriptor in each entry vector;
an eighth computation component operative to form an adjusted query vector by subtracting the mean value from its respective descriptor in the original query vector; and,
a ninth computation component operative to divide each descriptor in each new entry vector and in the adjusted query vector by its standard deviation.

32. The system of claim 29 further comprising computation components operative to standardize all of the entry vectors and all of the vectors of the set of query vectors.

33. The system of claim 32 wherein the computation components operative to standardize further comprise:
a tenth computation component operative to calculate a mean value for each descriptor of all the entry vectors;
an eleventh computation component operative to form new entry vectors for each entry in the database by subtracting the mean value from its respective descriptor in each entry vector;
a fourteenth computation component operative to form a supplemental set of query vectors by subtracting the mean value from its respective descriptor in each vector of the set of query vectors; and,
a fifteenth computation component operative to divide each descriptor in each new entry vector and in each vector of the supplemental set of query vectors by the standard deviation.

34. The system of claim 28, 29, 30, or 32 wherein the first input component is operative to accept the query datum from a user.

35. The system of claim 28, 29, 30, or 32 wherein the second input component is operative to accept the numeric weights from a user.

36. The system of claim 35 wherein the second input component comprises objects on a computer screen, said objects capable of being manipulated by the user to assign the weights.

37. The system of claim 36 wherein said objects comprise sliders with numeric scales.

38. The system of claim 36 wherein said objects comprise dials with numeric scales.

39. The system of claim 36 wherein said objects comprise text boxes allowing numeric entry.

40. The system of claim 28, 29, 30, or 32 wherein the fourth or eighth computational component is operative to calculate the similarity value using a weighted Euclidian Distance between any query vector and any entry vector.

41. The system of claim 28, 29, 30, or 32 wherein the fourth or eighth computational component is operative to calculate the similarity value using a weighted Hamming Distance between any query vector and any entry vector.

42. The system of claim 28, 29, 30, or 32 wherein the fourth or eighth computational component is operative to calculate the similarity value using a weighted Sorgel Distance between any query vector and any entry vector.

43. The system of claim 28, 29, 30, or 32 wherein the fourth or eighth computational component is operative to calculate the similarity value using a weighted Tanimoto Coefficient between any query vector and any entry vector.

44. The system of claim 28, 29, 30, or 32 wherein the fourth or eighth computational component is operative to calculate the similarity value using a weighted Dice Coefficient between any query vector and any entry vector.

45. The system of claim 28, 29, 30, or 32 wherein the fourth or eighth computational component is operative to calculate the similarity value using a weighted Cosine Coefficient between any query vector and any entry vector.

46. The system of claim 28, 29, 30, or 32 wherein said database entries are representative of chemical compounds.

47. The system of claim 46 wherein the first input component is operative to accept the query datum wherein said query datum is generated by a chemical structure drawing package.

48. The system of claim 46 further comprising a computational component operative to characterize the query datum and database entries by structure fragments.

49. The system of claim 48 wherein the structure fragments are contained within and referenced in an electronic dictionary.

50. The system of claim 46 further comprising a computational component operative to generate the structure fragments automatically.

51. A system for searching data comprising:
a) a storage device that stores an electronic database containing entries with characteristics capable of being represented by numeric descriptors;
b) a display device; and,
c) a processor programmed to:
   assign to each entry a numeric entry vector, the elements of which comprise descriptors that represent the characteristics in a predetermined order;
   accept a query to be compared with the entries;
   assign to the query, an original numeric query vector, the elements of which comprise descriptors that represent the characteristics in the predetermined order;
   accept a specification, for each element of the original query vector, of a numeric weight representing the relative importance of that characteristic to the other characteristics;
   construct a weight vector, each element of which is populated with the specified numeric weight that is representative of the characteristic represented in the corresponding element of the original query vector;
   calculate for each entry in the database a weighted similarity value using the original query vector, the entry vector, and the weight vector;
   order the entry vectors according to their similarity values; and,
   display the ordered entries on the display device.

52. The system of claim 51, wherein the processor is additionally programmed to:
analyze the query for the presence of characteristics having defined equivalents or variants, and if such equivalents or variants are found:
   create a set of numeric query vectors, consisting of one vector for each equivalent or variant, the elements of which comprise descriptors that represent the characteristics in the predetermined order, wherein descriptors that represent the equivalents or variants are substituted for their respective descriptors in the original query vector;
   calculate for each entry in the database a weighted similarity value using each vector of the set of query vectors, the entry vector, and the weight vector; and,
   merge and order the entries according to similarity values calculated using the original query vector and the set of query vectors.

53. The system of claim 51 wherein the processor is additionally programmed to standardize the original query vector and all of the entry vectors.

54. The system of claim 53, wherein the processor additionally programmed to standardize:
calculates a mean value and standard deviation for each descriptor of all the entry vectors;
forms new entry vectors for each entry in the database by subtracting the mean value from its respective descriptor in each entry vector;
forms an adjusted query vector by subtracting the mean value from its respective descriptor in the original query vector; and,
divides each descriptor in each new entry vector and the adjusted query vector by the standard deviation.

55. The system of claim 52 wherein the processor is additionally programmed to standardize all of the entry vectors and all of the vectors of the set of query vectors.

56. The system of claim 55, wherein the processor additionally programmed to standardize:
calculates a mean value and standard deviation for each descriptor of all the entry vectors;
forms new entry vectors for each entry in the database by subtracting the mean value from its respective descriptor in each entry vector;
forms a supplemental set of query vectors by subtracting the mean value from its respective descriptor in each vector of the set of query vectors; and,
divides each descriptor in each new entry vector and each vector of the supplemental set of query vectors by the standard deviation.

57. The system of claim 51, 52, 53, or 55 further comprising an input device that accepts input from a user.

58. The system of claim 57 wherein the query can be submitted by the user using the input device.

59. The system of claim 57 wherein the weights can be assigned by the user using the input device.

60. The system of claim 59 wherein the display device is a computer screen.

61. The system of claim 60 wherein the weights can be assigned by the user manipulating objects on the computer screen.

62. The system of claim 61 wherein said objects comprise dials with numeric scales.

63. The system of claim 61 wherein said objects comprise text boxes allowing numeric entry.

64. The system of claim 51, 52, 53, or 55 wherein said similarity value is calculated using a weighted Euclidean Distance between any query vector and any entry vector.

65. The system of claim 51, 52, 53, or 55 wherein said similarity value is calculated using a weighted Hamming Distance between any query vector and any entry vector.

66. The system of claim 51, 52, 53, or 55 wherein said similarity value is calculated using a weighted Sorgel Distance between any query vector and any entry vector.

67. The system of claim 51, 52, 53, or 55 wherein said similarity value is calculated using a weighted Tanimoto Coefficient between any query vector and any entry vector.

68. The system of claim 51, 52, 53, or 55 wherein said similarity value is calculated using a weighted Dice Coefficient between any query vector and any entry vector.

69. The system of claim 51, 52, 53, or 55 wherein said similarity value is calculated using a weighted Cosine Coefficient between any query vector and any entry vector.

70. A system for searching data comprising:
means for storing and maintaining an electronic database containing entries with characteristics that are capable of being represented by numeric descriptors;
means for assigning to each entry a numeric entry vector, the elements of which comprise descriptors that represent the characteristics in a predetermined order;
means for establishing a query to be compared with the entries;
means for assigning to the query, an original query vector, the elements of which comprise descriptors that represent the characteristics in the predetermined order;
means for specifying, for each element of the original query vector, a numeric weight representing the relative importance of that characteristic to the other characteristics;
means for constructing a weight vector, each element of which is populated with the specified numeric weight that is representative of the characteristic represented in the corresponding element of the original query vector;
means for calculating for each entry in the database a weighted similarity value using the query vector, the entry vector, and the weight vector;
means for ordering the entry vectors according to their similarity values; and,
means for displaying the ordered entries on the display device.

71. The system of claim 70 further comprising:
means for analyzing the query for the presence of characteristics having defined equivalents or variants;
means for creating a set of numeric query vectors, consisting of one vector for each equivalent or variant, if found, the elements of which comprise descriptors that represent the equivalents or variants, said descriptors being substituted for their respective descriptors in the original query vector;
means for calculating for each entry in the database a weighted similarity value using each vector of the set of query vectors, if any, the entry vector, and the weight vector; and,
means for merging and ordering the entries according to the similarity values calculated using the original query vector and the set of query vectors.

72. The system of claim 70 further comprising means for standardizing the original query vector and all of the entry vectors.

73. The system of claim 72 wherein means for standardizing further comprises:
means for calculating a mean value and standard deviation for each descriptor of all the entry vectors;
means for forming new entry vectors for each entry in the database by subtracting the mean value from its respective descriptor in each entry vector;
means for forming an adjusted query vector by subtracting the mean value from its respective descriptor in the original query vector; and,
means for dividing each descriptor in each new entry vector and the adjusted query vector by the standard deviation.

74. The system of claim 71 further comprising means for standardizing all of the entry vectors and all of the vectors of the set of query vectors.

75. The system of claim 74 wherein means for standardizing further comprises:
means for calculating a mean value and standard deviation for each descriptor of all the entry vectors;
means for forming new entry vectors for each entry in the database by subtracting the mean value from its respective descriptor in each entry vector;
means for forming a supplemental set of query vectors by subtracting the mean value from its respective descriptor in each vector of the set of query vectors; and,
means for dividing each descriptor in each new entry vector and each vector of the supplemental set of query vectors by the standard deviation.

76. The system of claim 70, 71, 72, or 74 further comprising a means to accept input from a user.

77. The system of claim 76 wherein the input from the user comprises the query.

78. The system of claim 76 wherein the input from the user comprises assignment of the numeric weights.

79. A computer-readable medium having computer-executable instructions for comparing entries within an electronic database, wherein the characteristics are capable of being represented by numeric descriptors, said instructions comprising:
assigning to each entry a numeric entry vector, the elements of which comprise descriptors that represent the characteristics in a predetermined order;
establishing a query to be compared with the entries;
assigning to the query, an original numeric query vector, the elements of which comprise descriptors that represent the characteristics in the predetermined order;
specifying, for each element of the original query vector, a numeric weight representing the relative importance of that characteristic to the other characteristics;
constructing a weight vector, each element of which is populated with the specified numeric weight that is representative of the characteristic represented in the corresponding element of the original query vector;
calculating for each entry in the database a weighted similarity value using the original query vector, the entry vector, and the weight vector;
ordering the entries according to their similarity values; and,
displaying the ordered entries.

80. The computer-readable medium of claim 79 further comprising computer-executable instructions that comprise:
creating a set of numeric query vectors, consisting of one vector for each equivalent or variant, the elements of which comprise descriptors that represent the characteristics in the predetermined order, wherein descriptors that represent the equivalents or variants are substituted for their respective descriptors in the original query vector;
calculating for each entry in the database a weighted similarity value using each vector of the set of query vectors, the entry vector, and the weight vector; and, merging and ordering the entries according to the similarity values calculated using the original query vector and the set of query vectors.

81. The computer-readable medium of claim 79 further comprising computer executable instructions to standardize the original query vector and all of the entry vectors.

82. The computer-readable medium of claim 81 wherein the computer-executable instructions to standardize comprise:
calculating a mean value and standard deviation for each descriptor of all the entry vectors;
forming new entry vectors for each entry in the database by subtracting the mean value from its respective descriptor in each entry vector;
forming an adjusted query vector by subtracting the mean value from its respective descriptor in the original query vector; and,
dividing each descriptor in each new entry vector and the adjusted query vector by the standard deviation.

83. The computer-readable medium of claim 80 further comprising computer-executable instructions to standardize all of the entry vectors and all of the vectors of the set of query vectors.

84. The computer-readable medium of claim 83 wherein the computer-executable instructions to standardize comprise:
calculating a mean value and standard deviation for each descriptor of all the entry vectors;
forming new entry vectors for each entry in the database by subtracting the mean value from its respective descriptor in each entry vector;
forming a supplemental set of query vectors by subtracting the mean value from its respective descriptor in each vector of the set of query vectors; and,
dividing each descriptor in each new entry vector and the each vector of the supplemental set of query vectors by the standard deviation.

85. The computer-readable medium of claim 79, 80, 81, or 83 having computer-executable instructions that permit the numeric weights to be assigned by a user.

86. The computer-readable medium of claim 85 having computer-executable instructions that permit the user to assign the numeric weights by manipulating objects on a computer screen.

87. The computer-readable medium of claim 86 having computer-executable instructions wherein said objects comprise sliders with numeric scales.

88. The computer-readable medium of claim 86 having computer-executable instructions wherein said objects comprise dials with numeric scales.

89. The computer-readable medium of claim 86 having computer-executable instructions wherein said objects comprise text boxes allowing numeric entry.

90. The computer-readable medium of claim 85 having computer-executable instructions wherein, following display of the ordered entries, said method further comprises:
re-specifying, for each characteristic of the query, a new numeric weight representing a refined relative importance of that characteristic to the other characteristics;
constructing a new weight vector, the elements of which are populated with the new weights which are representative of the characteristics in the predetermined order;
re-calculating for each entry a new similarity value;
re-ordering the entries according to their new similarity values;
displaying the re-ordered entries; and,
repeating the above actions as often as desired by the user.

91. The computer-readable medium of claim 79, 80, 81, or 83 having computer-executable instructions wherein said similarity value is calculated using a weighted Euclidean Distance between any query vector and any entry vector.

92. The computer-readable medium of claim 79, 80, 81, or 83 having computer-executable instructions wherein said similarity value is calculated using a weighted Hamming Distance between any query vector and any entry vector.

93. The computer-readable medium of claim 79, 80, 81, or 83 having computer-executable instructions wherein said similarity value is calculated using a weighted Sorgel Distance between any query vector and any entry vector.

94. The computer-readable medium of claim 79, 80, 81, or 83 having computer-executable instructions wherein said similarity value is calculated using a weighted Tanimoto Coefficient between any query vector and any entry vector.

95. The computer-readable medium of claim 79, 80, 81, or 83 having computer-executable instructions wherein said similarity value is calculated using a weighted Dice Coefficient between any query vector and any entry vector.

96. The computer-readable medium of claim 79, 80, 81, or 83 having computer-executable instructions wherein said similarity value is calculated using a weighted Cosine Coefficient between any query vector and any entry vector.

97. The computer-readable medium of claim 79, 80, 81, or 83 having computer-executable instructions wherein each element of each query vector and of each entry vector is either one or zero thereby forming binary vectors.

98. The computer-readable medium of claim 79, 80, 81, or 83 having computer-executable instructions wherein said database entries and said query are representative of structures of chemical compounds.

99. The computer-readable medium of claim 98 having computer-executable instructions that permit the query to be generated by a chemical structure drawing package.

100. The computer-readable medium of claim 98 having computer-executable instructions wherein the characteristics of the query and the database entries are characterized by structure fragments.

101. The computer-readable medium of claim 100 having computer-executable instructions wherein the query vector and all entry vectors are binary vectors indicating the presence or absence of said structure fragments.

102. The computer-readable medium of claim 100 having computer-executable instructions wherein the structure fragments are contained within and referenced in an electronic dictionary.

103. The computer-readable medium of claim 100 having computer-executable instructions wherein the structure fragments are generated automatically.

104. The computer-readable medium of claim 79, 80, 81, or 83 having computer-executable instructions wherein the characteristics associated with said database entries are representative of biological activity screening results and wherein the characteristics associated with said query are also representative of biological activity screening results.

105. The computer-readable medium of claim 79, 80, 81, or 83 having computer-executable instructions for storing a representation of the ordering for further use.

* * * * *